United States Patent
Yamaguchi et al.

(10) Patent No.: US 9,095,477 B2
(45) Date of Patent: Aug. 4, 2015

(54) NON-WOVEN SHEET, MANUFACTURING METHOD THEREOF AND ABSORBENT ARTICLE

(75) Inventors: Masashi Yamaguchi, Kagawa (JP); Toru Oba, Kagawa (JP); Akihiro Kimura, Kagawa (JP); Katsuhiro Uematsu, Kagawa (JP)

(73) Assignee: Unicharm Corporation, Ehime (JP)

( * ) Notice: Subject to any disclaimer, the term of this patent is extended or adjusted under 35 U.S.C. 154(b) by 158 days.

(21) Appl. No.: 13/819,724

(22) PCT Filed: Jun. 21, 2011

(86) PCT No.: PCT/JP2011/064618
§ 371 (c)(1), (2), (4) Date: Feb. 28, 2013

(87) PCT Pub. No.: WO2012/029391
PCT Pub. Date: Mar. 8, 2012

(65) Prior Publication Data
US 2013/0158497 A1    Jun. 20, 2013

(30) Foreign Application Priority Data
Aug. 31, 2010    (JP) ................................ 2010-194229

(51) Int. Cl.
*A61F 13/15*    (2006.01)
*A61F 13/511*    (2006.01)
(Continued)

(52) U.S. Cl.
CPC ......... *A61F 13/51108* (2013.01); *A61F 13/512* (2013.01); *A61F 13/5121* (2013.01);
(Continued)

(58) Field of Classification Search
CPC .............. A61F 13/51; A61F 13/51104; A61F 13/51108; A61F 13/512; A61F 13/5121; A61F 13/5126; A61F 2013/51078; A61F 2013/5108; A61F 2013/51083; A61F 2013/51085; B32B 3/26; B32B 3/263; B32B 3/266; B32B 3/28; B32B 3/30

USPC ................... 604/379, 380, 383; 428/167, 169
See application file for complete search history.

(56) References Cited

U.S. PATENT DOCUMENTS 5,536,555 A * 7/1996 Zelazoski et al. ............. 428/138
5,895,380 A * 4/1999 Turi et al. ...................... 604/383
(Continued)

FOREIGN PATENT DOCUMENTS

EP      2 034 071 A1    3/2009
JP      2007-167212 A    7/2007
(Continued)

OTHER PUBLICATIONS

International Search Report from corresponding PCT application No. PCT/JP2011/064618 dated Sep. 20, 2011 (5 pgs).

*Primary Examiner* — Lynne Anderson
(74) *Attorney, Agent, or Firm* — Brinks Gilson & Lione

(57) ABSTRACT

A nonwoven sheet for use in absorbent articles such as disposable diapers which is capable of reducing the range of surface diffusion of, and reducing re-adhesion to the skin of, highly viscous fluid excretion. The nonwoven sheet has mutually perpendicular longitudinal, transverse and thickness directions, and has in the aforementioned thickness direction a front surface and a back surface opposite thereof. Ridges and grooves are formed alternately so as to extend in parallel in the aforementioned longitudinal direction and so as to form repeated undulations in the aforementioned transverse direction. The nonwoven sheet has a bottom surface which, when the aforementioned nonwoven sheet is placed on a horizontal surface with the back surface (opposite of the front surface in contact with the skin of the wearer) down, is the surface that contacts the aforementioned horizontal surface. On the back surface of the aforementioned grooves are formed in the aforementioned longitudinal direction alternately areas where the height from the bottom surface is relatively high and parts corresponding to the bottom surface. Openings are formed at least in the areas where the height from the bottom surface is relatively high, and a space is provided below said openings.

12 Claims, 19 Drawing Sheets

(51) Int. Cl.

| | | |
|---|---|---|
| *A61F 13/512* | (2006.01) | |
| *B32B 3/30* | (2006.01) | |
| *B32B 3/26* | (2006.01) | |
| *B32B 3/28* | (2006.01) | |
| *D04H 1/54* | (2012.01) | |
| *D04H 1/70* | (2012.01) | |
| *D04H 1/425* | (2012.01) | |
| *D04H 1/4258* | (2012.01) | |
| *D04H 1/4266* | (2012.01) | |
| *D04H 1/541* | (2012.01) | |
| *D01G 15/00* | (2006.01) | |
| *D04H 1/49* | (2012.01) | |
| *A61F 13/51* | (2006.01) | |

(52) U.S. Cl.
CPC ....... *A61F13/5126* (2013.01); *A61F 13/51104* (2013.01); *B32B 3/263* (2013.01); *B32B 3/266* (2013.01); *B32B 3/28* (2013.01); *B32B 3/30* (2013.01); *D01G 15/00* (2013.01); *D04H 1/425* (2013.01); *D04H 1/4258* (2013.01); *D04H 1/4266* (2013.01); *D04H 1/49* (2013.01); *D04H 1/54* (2013.01); *D04H 1/541* (2013.01); *D04H 1/70* (2013.01); *A61F 2013/51078* (2013.01)

(56) References Cited

U.S. PATENT DOCUMENTS

| | | | | |
|---|---|---|---|---|
| 6,093,871 | A * | 7/2000 | Takai et al. | 604/383 |
| 6,642,432 | B1 * | 11/2003 | Matsui et al. | 604/380 |
| 8,450,556 | B2 * | 5/2013 | Miyamoto et al. | 604/380 |
| 8,450,557 | B2 * | 5/2013 | Nishitani et al. | 604/380 |
| 2006/0247590 | A1* | 11/2006 | Ito et al. | 604/379 |
| 2007/0298220 | A1 | 12/2007 | Noda et al. | |
| 2007/0298671 | A1 | 12/2007 | Noda et al. | |
| 2009/0221979 | A1* | 9/2009 | Huang et al. | 604/367 |
| 2010/0191207 | A1 | 7/2010 | Oba et al. | |
| 2013/0034686 | A1* | 2/2013 | Mitsuno | 428/131 |

FOREIGN PATENT DOCUMENTS

| | | |
|---|---|---|
| JP | 2008-25084 A | 2/2008 |
| JP | 2008-025084 A | 2/2008 |
| JP | 2008-127706 A | 6/2008 |
| JP | 2009-030218 A | 2/2009 |
| JP | 2009-30218 A | 2/2009 |
| JP | 2010-024573 | 2/2010 |
| JP | 2010-106430 A | 5/2010 |

* cited by examiner

Fig.11
(a)
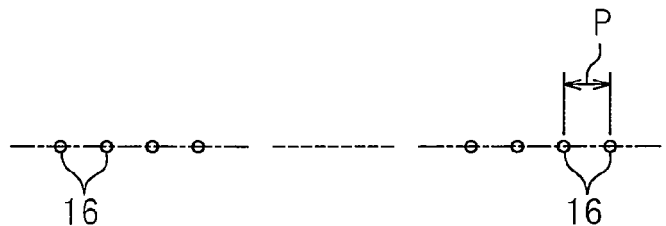
(b)
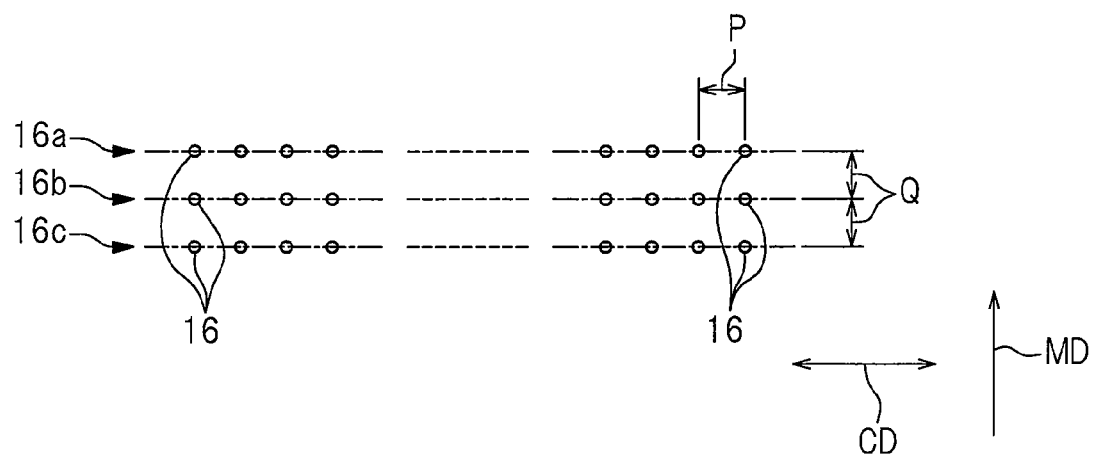
Fig.12
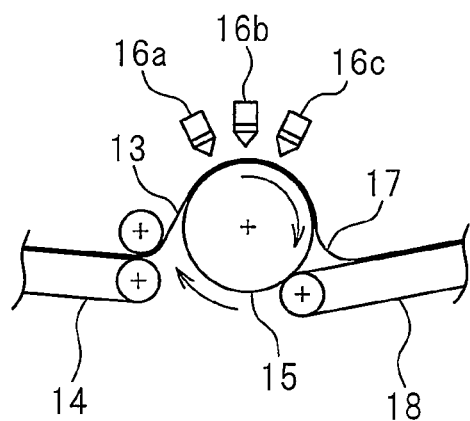

Fig. 14
(a)
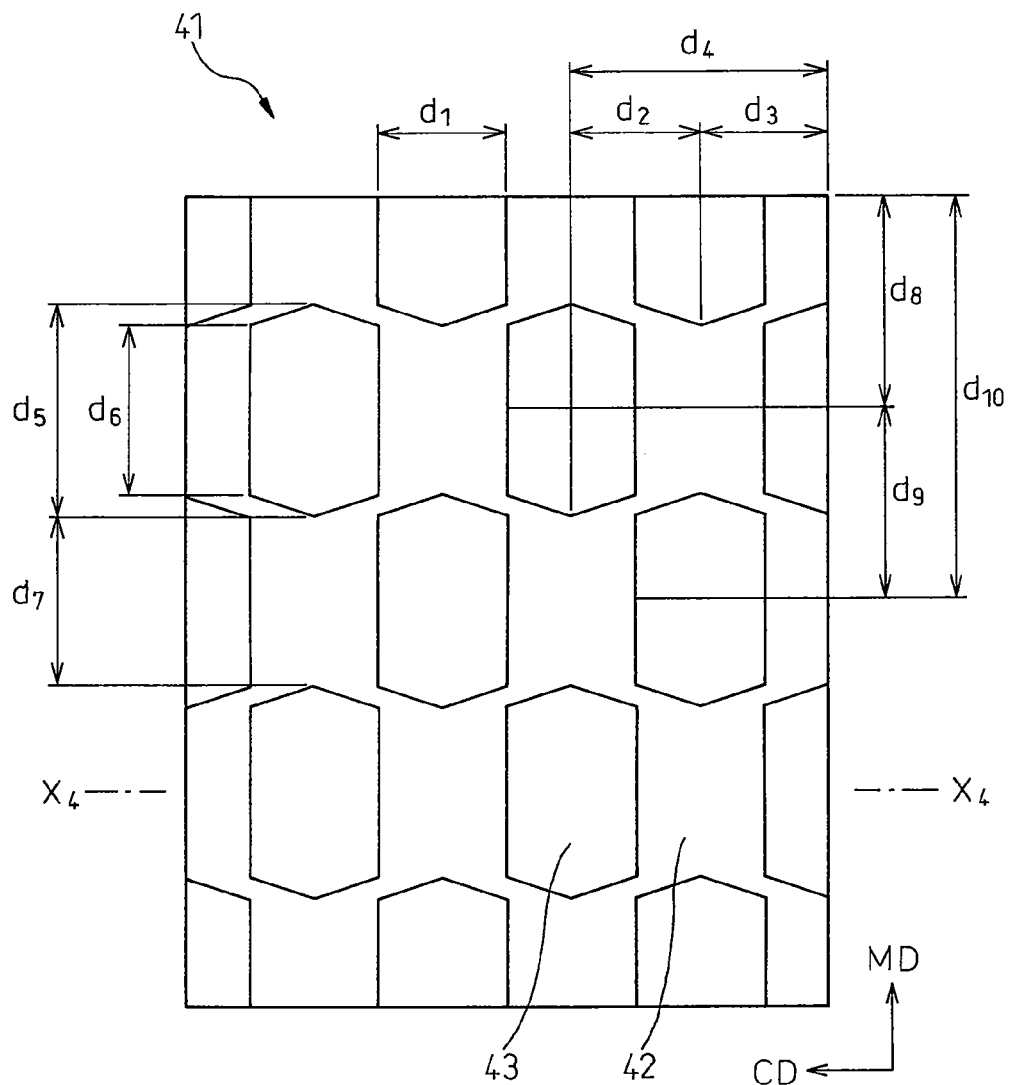
(b)
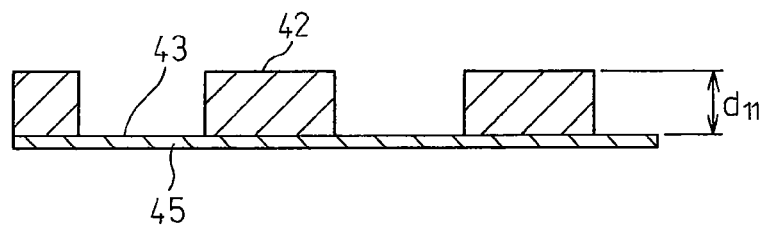

Fig.15
(a)
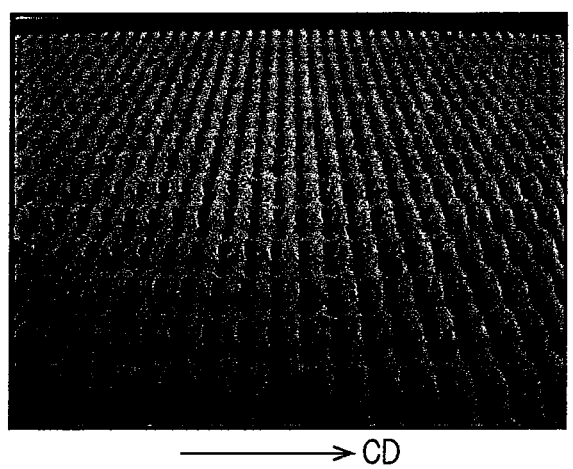
(b)
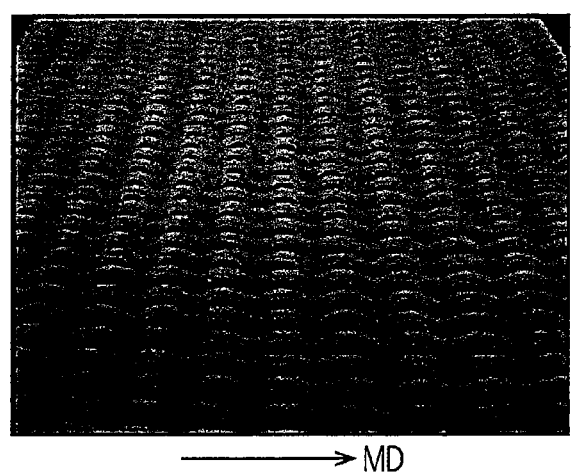

Fig.16
(a)
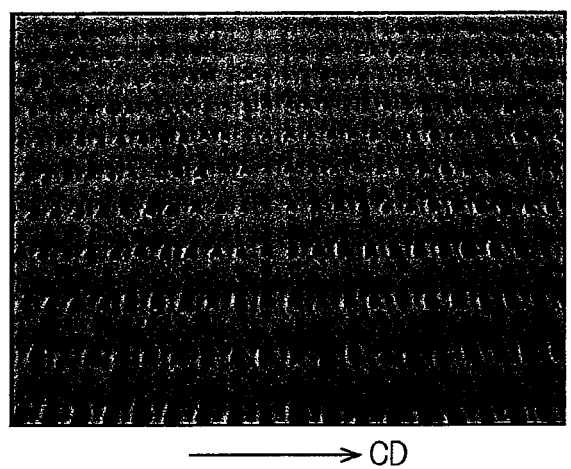
→ CD
(b)
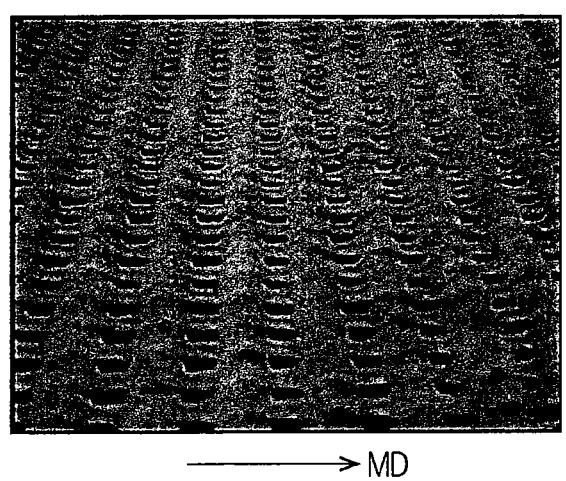
→ MD

→ CD

→ CD

NON-WOVEN SHEET, MANUFACTURING METHOD THEREOF AND ABSORBENT ARTICLE

RELATED APPLICATION

This application is a 35 U.S.C. §371 national phase filing of International Patent Application No. PCT/JP2011/064618, filed Jun. 21, 2011, through which and to which priority is claimed under 35 U.S.C. §119 to Japanese Patent Application No. 2010-194229, filed Aug. 31, 2010.

TECHNICAL FIELD

The present invention relates to a non-woven fabric sheet, a manufacturing method thereof and an absorbent article. More particularly, the present invention relates to a non-woven fabric sheet for an absorbent article such as a disposable diaper, a manufacturing method thereof, and an absorbent article that uses the non-woven fabric sheet.

BACKGROUND ART

Japanese Unexamined Patent Publication No. 2008-127706 discloses a sheet that prevents the return of liquids, which makes it difficult for a liquid to return to the skin side once it has been absorbed, dryness that does not allow liquid to be retained on the skin, wearability that does not cause a sense of discomfort when worn, and opacity that conceals the color of an absorbed liquid so as not to appear on the surface. This sheet is a corrugated sheet in which a plurality of grooves and ridges, respectively extending in one direction, are formed in a non-woven fabric, and the grooves and ridges are alternately arranged and mutually in parallel. The bottom portions of the grooves are flat over the direction in which they extend, and a plurality of openings are formed at prescribed intervals in the bottom portions. The ridges are formed convexly protruding from the back surface side towards the front surface side thereof in the form of projections, and the back sides of the non-woven fabric are in mutual contact at least at the bases of the protruding sites.

Japanese Unexamined Patent Publication No. 2007-167212 discloses a three-dimensional porous sheet capable of controlling the direction of diffusion of a liquid from ridges and facilitating bending of the ridges in the lengthwise direction. A plurality of ridges are formed in this sheet, openings are formed between mutually adjacent ridges, and sites that are relatively high and sites that are relatively low are alternately formed in the ridges in the lengthwise direction of the ridges.

DISCLOSURE OF THE INVENTION

Problems to be Solved by the Invention

In the sheet disclosed in Japanese Unexamined Patent Publication No. 2008-127706, since the bottoms of grooves are flat over the direction in which they extend, and a plurality of openings are formed in the bottom portions at prescribed intervals, the contact area between the bottom portions and an absorbent body and the like located there below increases, the openings are substantially covered, and a highly viscous liquid such as soft stool cannot be expected to permeate by using the openings.

Since the sheet disclosed in Japanese Unexamined Patent Publication No. 2007-167212 controls the direction of liquid diffusion with ridges, and diffusion of liquid occurs on the side that contacts the skin, there is the risk of the skin being soiled over a wide range.

Means for Solving the Problems

The present invention solves the aforementioned problems with a non-woven fabric sheet for an absorbent article, in which continuous surface irregularities are formed on the surface side that faces the skin side when worn, by providing openings in the vicinity of intermediate points in the height of projections between adjacent projections and providing a space below the openings. The term "openings" not only refers to portions in which fibers are completely absent, but rather is also used in the sense of being portions in which fibers are scarcely present to a degree that highly viscous liquid excrement is able to easily pass through.

The first subject invention is a non-woven fabric sheet having mutually perpendicular longitudinal, transverse and thickness directions, having a front surface and an opposing surface thereto in the form of a back surface in the direction of thickness, and having ridges and grooves alternately formed so as to extend mutually in parallel in the longitudinal direction so as to form repeated undulations in the transverse direction; wherein, the non-woven fabric sheet has a bottom surface that contacts a horizontal surface when placed on the horizontal surface with the back surface, which is the opposing surface of the front surface that contacts the skin of a wearer, facing down, sites where the height from the bottom surface is relatively high and low sites corresponding to the bottom surface are alternately formed along the longitudinal direction on the back surface of the grooves, openings are formed at least in the sites where the height from the bottom surface is relatively high, and a space is provided below the openings.

Preferably, the space provided below the openings is at least partially connected with a space provided below an adjacent opening.

Preferably, the portion corresponding to the bottom surface has a site having a relatively high basis weight and a site having a relatively low basis weight.

Preferably, the back surface of the non-woven fabric sheet has a bottom surface $B_0$ and surface $B_1$ of a height $b_1$ from the bottom surface, the bottom surface $B_0$ extends in a transverse direction perpendicular to the longitudinal direction and each bottom surface $B_0$ is arranged in parallel, and the space is connected in the transverse direction perpendicular to the longitudinal direction.

Preferably, sites where the height from the bottom surface is relatively high and relatively low sites are alternately formed along the longitudinal direction on the front surface of the ridges, a space is present below the relatively high sites of the ridges, and the height of the space from the bottom surface is $b_1$.

Preferably, the back surface of the non-woven fabric sheet has a bottom surface $B_0$ and a surface $B_1$ of a height $b_1$ from the bottom surface, the bottom surface $B_0$ and the surface $B_1$ are arranged in a staggered pattern, each bottom surface $B_0$ is separated from the adjacent bottom surface $B_0$, and each surface $B_1$ is connected to four adjacent surfaces $B_1$.

Preferably, each bottom surface $B_0$ has a shape selected from the group consisting of square, rectangular, rhomboid, polygonal, circular and oval shapes.

The second subject invention is a method for manufacturing a non-woven fabric sheet, comprising: a) a step for obtaining a web by opening a fiber assembly by passing through a carding machine, b) a step for placing the web obtained in step a) on a pattern plate, on which convex portions having a comparatively large air flow resistance and concave portions having a comparatively small air flow resistance are arranged in a regular pattern, and spraying a fluid onto the web from a plurality of nozzles arranged in a row in a cross-machine direction perpendicular to a machine direction while transporting over the pattern plate, and c) a step for heating the web and fusing at sites where fibers are mutually intersecting.

Preferably, the pattern plate has a large number of convex portions extending in parallel in the cross-machine direction.

Preferably, the pattern plate has a large number of concave portions arranged in a staggered pattern.

A third subject invention is an absorbent article that uses the aforementioned non-woven fabric sheet.

Effects of the Invention

Since the non-woven fabric sheet of the present invention has openings formed at a location higher than a horizontal surface when the non-woven fabric sheet is placed on the horizontal surface with the back surface thereof, which is the opposing surface of the front surface that contacts the skin of a wearer, facing down, and has an opening provided below the openings, the volume of a highly viscous excrement liquid introduced below the openings can be increased, the range over which a highly viscous excrement liquid, in the manner of watery stool produced by newborn infants, diffuses on the front side can be decreased, and the amount that re-adheres to the skin can be reduced.

BRIEF DESCRIPTION OF THE DRAWINGS

FIG. 11 is a drawing showing an example of the arrangement of nozzles used in step b.

FIG. 12 is a drawing showing an example of multiple rows of nozzles used in step b.

FIG. 14 is a drawing showing another example of a pattern plate.

FIG. 15 depicts photographs of the front surface of the non-woven fabric sheet of Example 1.

FIG. 16 depicts photographs of the back surface of the non-woven fabric sheet of Example 1.

EMBODIMENTS OF THE INVENTION

Figure 1:
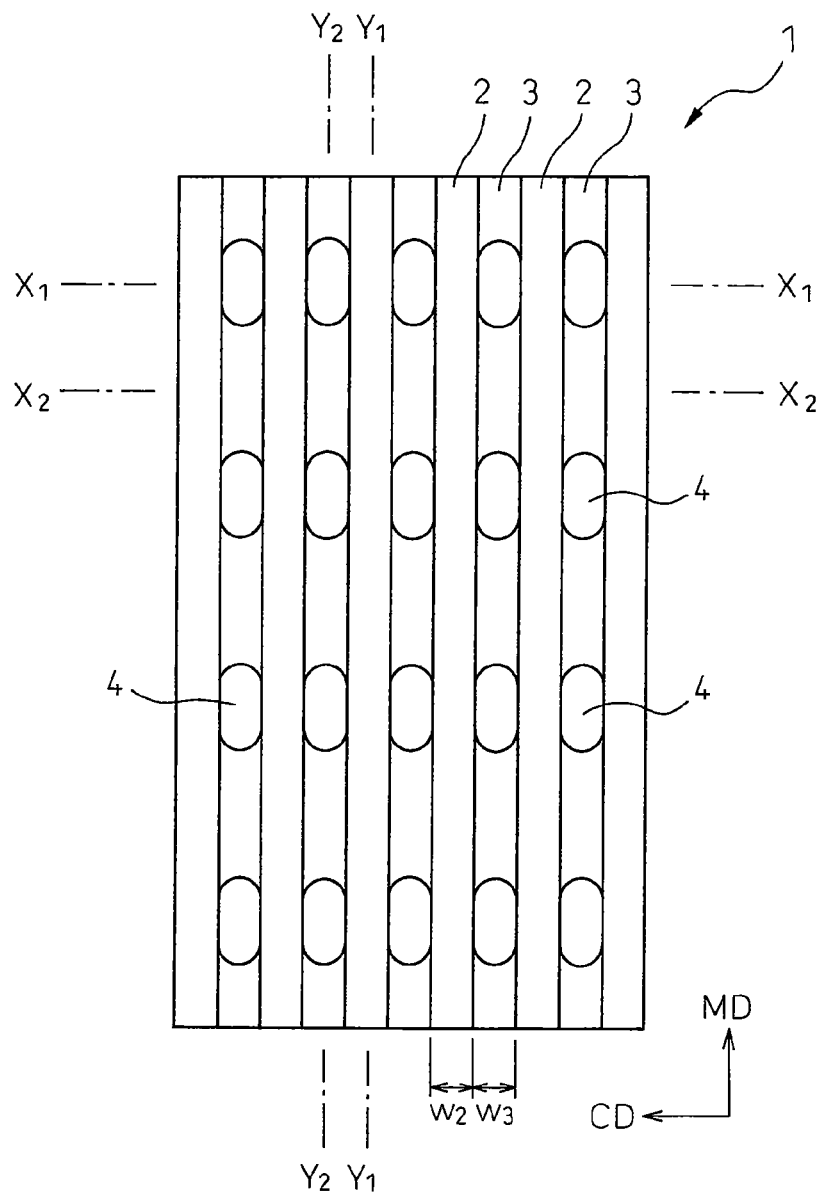
FIG. 1 is an enlarged schematic drawing of an overhead view of a first embodiment of the non-woven fabric sheet of the present invention.

Although the following provides an explanation of embodiments of the present invention with reference to the drawings, the present invention is not limited to the embodiments shown in the drawings.

FIG. 1 is an enlarged schematic drawing of an overhead view of a first embodiment of the non-woven fabric sheet of the present invention.

Figure 2:
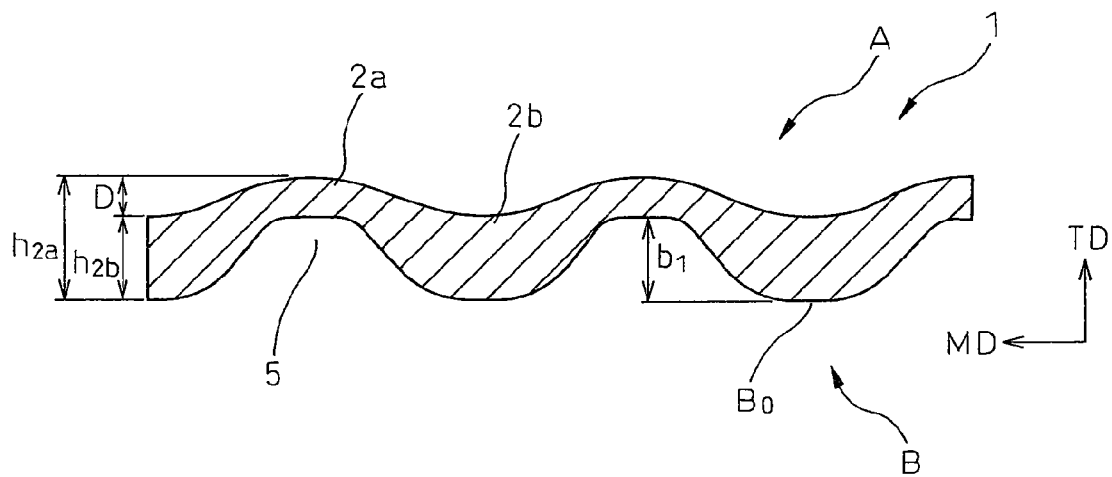
FIG. 2 is an enlarged schematic drawing of a cross-sectional view taken along line $Y_1$-$Y_1$ of FIG. 1.

FIG. 2 is an enlarged schematic drawing of a cross-sectional view taken along line $Y_1$-$Y_1$ of FIG. 1.

Figure 3:
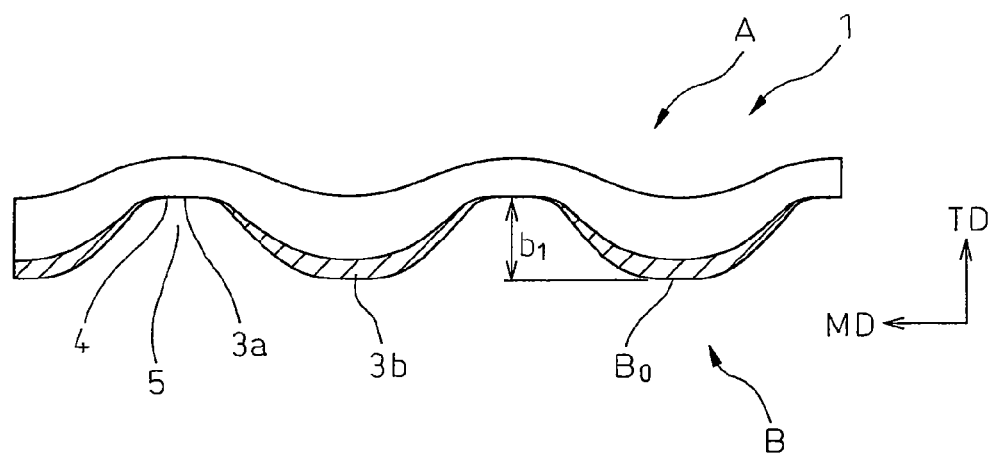
FIG. 3 is an enlarged schematic drawing of a cross-sectional view taken along line $Y_2$-$Y_2$ of FIG. 1.

FIG. 3 is an enlarged schematic drawing of a cross-sectional view taken along line $Y_2$-$Y_2$ of FIG. 1.

Figure 4:
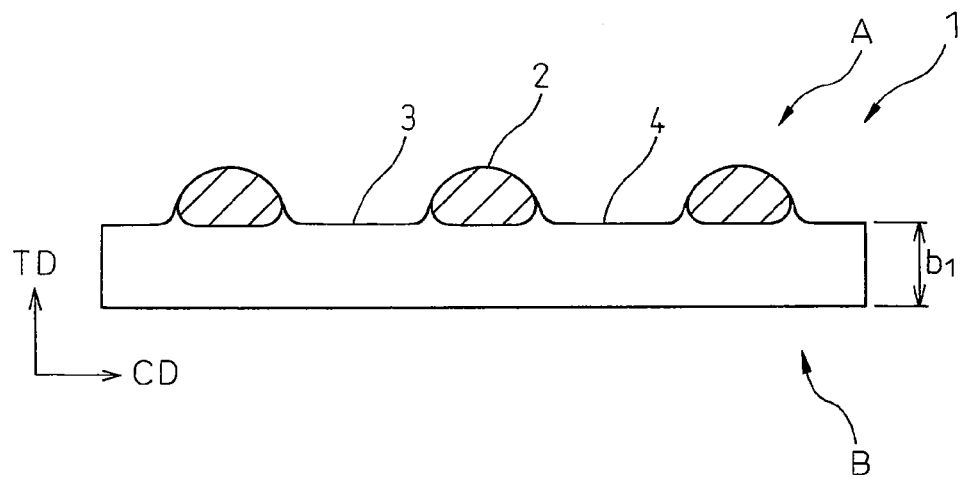
FIG. 4 is an enlarged schematic drawing of a cross-sectional view taken along line $X_1$-$X_1$ of FIG. 1.

FIG. 4 is an enlarged schematic drawing of a cross-sectional view taken along line $X_1$-$X_1$ of FIG. 1.

Figure 5:
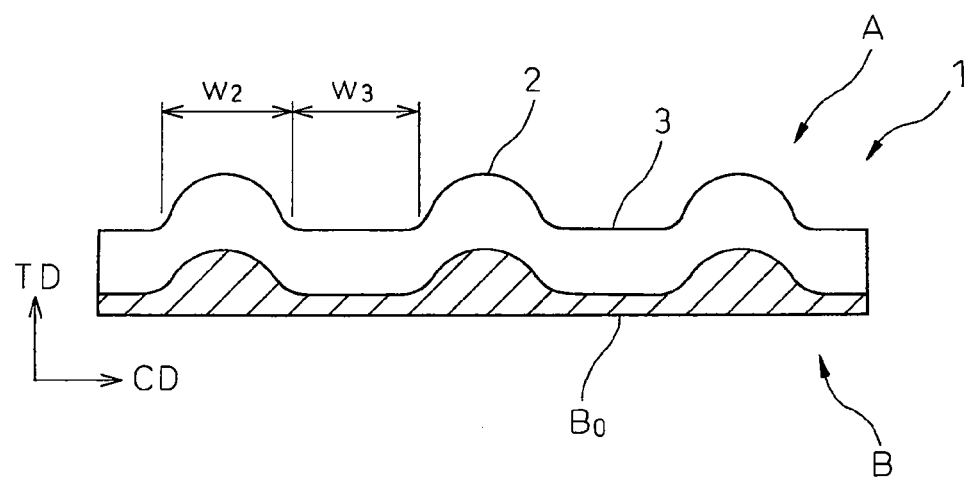
FIG. 5 is an enlarged schematic drawing of a cross-sectional view taken along line $X_2$-$X_2$ of FIG. 1.

FIG. 5 is an enlarged schematic drawing of a cross-sectional view taken along line $X_2$-$X_2$ of FIG. 1.

A non-woven fabric sheet 1 has mutually perpendicular longitudinal, transverse and thickness directions, and has a front surface A and a back surface B on the opposite side there from in the direction of thickness. The front surface A is a surface that contacts the skin of a wearer of an absorbent article in the case the non-woven fabric sheet 1 is incorporated by arranging more on an upper surface side than a back surface side, such as by arranging as a top sheet or second sheet on an absorbent article such as a disposable diaper or sanitary napkin, or by arranging in a portion that passes through an absorbent body. The back surface B is a surface that is on the opposite side from the front surface that contacts the skin of a wearer.

In the non-woven fabric sheet 1, ridges 2 and grooves 3 are formed in alternate rows so as to form repeated undulations in a transverse direction extending mutually in parallel in a longitudinal direction.

The longitudinal direction coincides with a machine direction in a non-woven fabric sheet manufacturing process to be subsequently described, while the transverse direction coincides with a cross-machine direction in the non-woven fabric sheet manufacturing process to be subsequently described. In the following descriptions, the longitudinal direction is referred to as MD, the transverse direction as CD, and the thickness direction as TD.

The non-woven fabric sheet 1 has bottom surfaces $B_0$ that contact a horizontal surface when the non-woven fabric sheet 1 is placed on the horizontal surface with the back surface B facing down. Sites 3a where the height from the bottom surfaces $B_0$ (height from the horizontal surface) is relatively high and low sites 3b corresponding to the bottom surfaces are alternately formed in the longitudinal direction as shown in FIG. 3 on the back surface B of the grooves 3. Openings 4 are at least formed in the sites 3a where the height from the bottom surfaces is relatively high, and a space 5 is provided below the openings 4. The term "openings" not only refers to portions where fibers are completely absent, but is also used in the sense of being portions where fibers are scarcely present to a degree that highly viscous liquid excrement is able to easily pass through. Fibers being scarcely present refers to, for example, a space area ratio of 15% or more as determined according to the prescribed method described below.

Space area ratio can be measured using the method indicated below.

(1) An image of the side of the sheet that faces the skin side when worn is scanned with a scanner with a black mount placed in the background.

(2) Image analysis software in the form of USB Digital Scale (Scalar Corp.) is then started up and the image scanned in (1) is loaded.

(3) After having set binarization to 0 to 150, the scanned image undergoes image conversion by static binarization.

(4) A site on the grooves where the height from the bottom surfaces is relatively high is arbitrarily selected, and the range of that site is specified.

(5) The shape characteristic extraction command is selected, black is selected for the target color in the count tab, the width and height of the extraction target is specified to 0 pixels or more, and the count button is pressed to extract a void portion.

(6) Continuing, total area is specified with the extracted volume tab, and the feature value button is pressed to measure the total hole area (black portion) within the specified range.

(7) The space area ratio is then calculated according to the formula indicated below.

Space area ratio=Total hole area (black portion) within specified range/area of specified range (8) Measurements obtained from at least 20 points using the method described above are then averaged, and the resulting average value is used.

Figure 17:
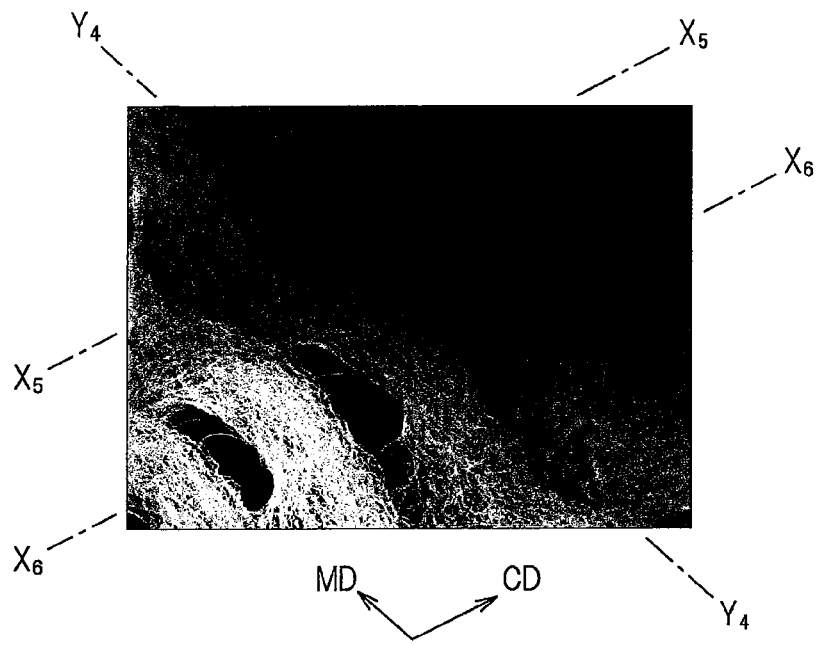
FIG. 17 is a photograph of an enlarged perspective view of the essential portion of the non-woven fabric sheet of Example 1.
Figure 18:
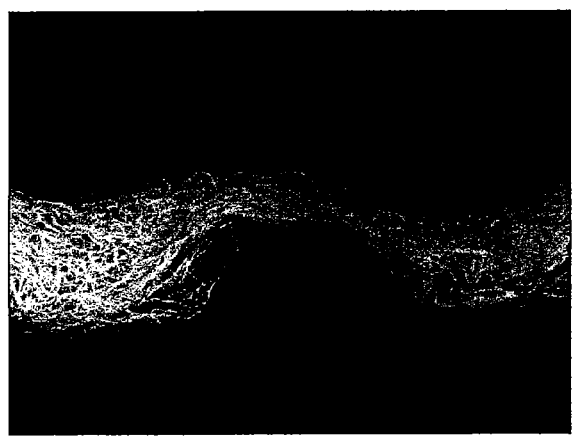
FIG. 18 is a photograph of a cross-section taken along line $Y_4$-$Y_4$ of FIG. 17.
Figure 19:
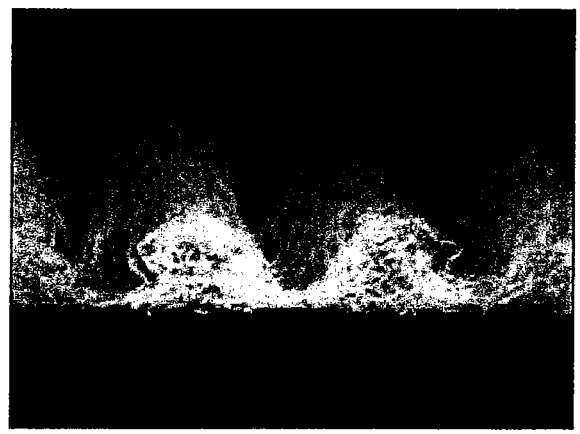
FIG. 19 is a photograph of a cross-section taken along line $X_5$-$X_5$ of FIG. 17.
Figure 20:
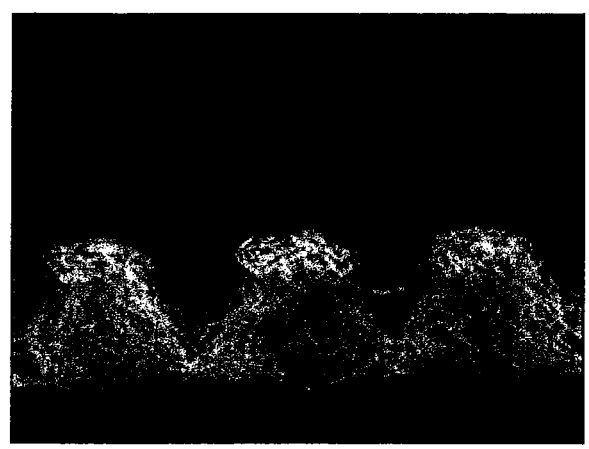
FIG. 20 is a photograph of a cross-section taken along line $X_6$-$X_6$ of FIG. 17.

FIG. 17 is a photograph of an enlarged perspective view of the essential portion of the non-woven fabric sheet of a first embodiment. FIG. 18 is a photograph of a cross-section taken along line $Y_4$-$Y_4$ of FIG. 17 (taken along the longitudinal direction of the grooves 3), FIG. 19 is a photograph of a cross-section taken along line $X_5$-$X_5$ of FIG. 17 (taken along the transverse direction and passing through sites corresponding to the bottom surfaces $B_0$), and FIG. 20 is a photograph of a cross-section taken along line $X_6$-$X_6$ of FIG. 17 (taken along the transverse direction and passing through apices of the ridges 2).

Although a structure is employed in which the space 5 is formed below the openings 4, from the viewpoint of enabling the movement of liquid on the side of the back surface B of the non-woven fabric sheet and preventing liquid from leaking back to the front side, at least a portion of the space 5 provided below the openings 4 is preferably connected to the adjacent space 5 provided below the openings 4. In the non-woven fabric sheet of the first embodiment, the space 5 is arranged across the transverse direction perpendicular to the longitudinal direction in which the ridges 2 and the grooves 3 extend.

The back surface B of the non-woven fabric sheet of the first embodiment has bottom surfaces $B_0$ and surfaces $B_1$ of a height $b_1$ from the bottom surfaces $B_0$, and the bottom surfaces $B_0$ extend in the transverse direction, each of the bottom surfaces $B_0$ are arranged in parallel, and the space 5 is connected in the transverse direction. The height of the space 5 from the aforementioned horizontal surface is $b_1$.

In addition, the bottom surfaces $B_0$ of the non-woven fabric sheet are preferably provided with sites where the basis weight is partially adjusted higher from the viewpoint of preventing the sheet from compressing and expanding due to the effects of line tension and the like during manufacturing and preventing the space provided below the openings, formed at sites where the height from the bottom surfaces is relatively high, from being crushed.

Sites 2a where the height from the bottom surfaces is relatively high and relatively low sites 2b are alternately formed along the longitudinal direction on the front surface of the ridges 2 of the non-woven fabric sheet of the first embodiment, the space 5 is present below the sites 2a where the height from the bottom surfaces is relatively high between the non-woven fabric and the aforementioned horizontal surface, and the height of the space 5 from the above-mentioned horizontal surface (namely, the height from the bottom surfaces $B_0$) is $b_1$.

A height $h_{2a}$ from the bottom surfaces of the surfaces on the front surface side of the relatively high sites 2a is preferably 0.8 mm to 20 mm and more preferably 1.2 mm to 7 mm from the viewpoints of reducing rewetting of highly viscous excrement liquid in the non-woven fabric sheet 1 and feeling of use when worn. In the case of exceeding these ranges, product thickness becomes excessively thick when installing in a product, and the feeling of use when worn ends up increasing. In addition, in the case of being below these ranges, re-adherence to the skin cannot be reduced since the highly viscous liquid is not adequately separated from the skin.

A height $b_1$ (location of the openings 4) from the bottom surfaces of the relatively high sites 3a of the back surface of the grooves 3 (see FIG. 3) is preferably 0.5 mm to 15 mm and more preferably 1 mm to 5 mm from the viewpoint of providing the space 5 for introducing highly viscous excrement liquid below the openings 4. In the case of exceeding these ranges, since the ridge height inevitably ends up becoming excessively high, product thickness when installed in a product becomes excessively thick and feeling of use when worn ends up increasing. In addition, in the case of being below these ranges, the retention volume formed below the openings 4 is inadequate.

In addition, although the height of the ridges 2 may be constant over the longitudinal direction, sites 2a where the height from the bottom surfaces is relatively high and relatively low sites 2b are preferably alternately formed along the longitudinal direction on the front surface of the ridges 2 as shown in FIG. 2 from the viewpoints of increasing the space that separates the highly viscous liquid from the skin and the feeling of use when wearing in the case highly viscous liquid unable to be completely introduced below the openings has overflowed back to the skin side. A height difference D between a height $h_{2a}$ from the bottom surfaces of the surface on the front sides of the relatively high sites 2a and a height $h_{2b}$ from the bottom surfaces of the surface on the front sides of the relatively low sites 2b in this case is preferably 0.5 mm to 15 mm and more preferably 1 mm to 5 mm. In the case of exceeding these ranges, the ridge height inevitably becomes excessively high, product thickness when installed in a product becomes excessively thick, and the feeling during use when wearing ends up increasing. In addition, in the case of being below these ranges, there is hardly any increase in the space separating the highly viscous liquid and the skin.

Height (thickness) and height difference are measured using a CCD laser displacement gauge.

In addition, a width $w_2$ of the ridges 2 in the transverse direction of the non-woven fabric 1 is preferably 1 to 10 mm and more preferably 2 mm to 5 mm from the viewpoints of separating highly viscous liquid from the skin and moldability. In the case of exceeding these ranges, highly viscous liquid remains at a location close to the skin since regions where highly viscous liquid adhere to the ridges increases, thereby preventing re-adherence to the skin from being reduced. In addition, in the case of being below these ranges, molding of the irregular surface structure ends up becoming difficult.

A width $w_3$ in the transverse direction of the non-woven fabric sheet 1 is preferably 0.5 mm to 7 mm and more preferably 1 mm to 3 mm from the viewpoints of introducing a highly viscous liquid through openings formed in the grooves and separating highly viscous liquid from the skin. In the case of exceeding these ranges, there is increased susceptibility of the base material arranged on the skin and upper layer side digging into the grooves 3, and since regions where highly viscous liquid is separated from the skin become smaller as a result thereof, re-adherence to the skin cannot be reduced. In addition, in the case of being below these ranges, it ends up becoming difficult to introduce highly viscous liquid into the space below the openings.

Next, an explanation is provided of a second embodiment of the non-woven fabric sheet of the present invention.

Figure 6:
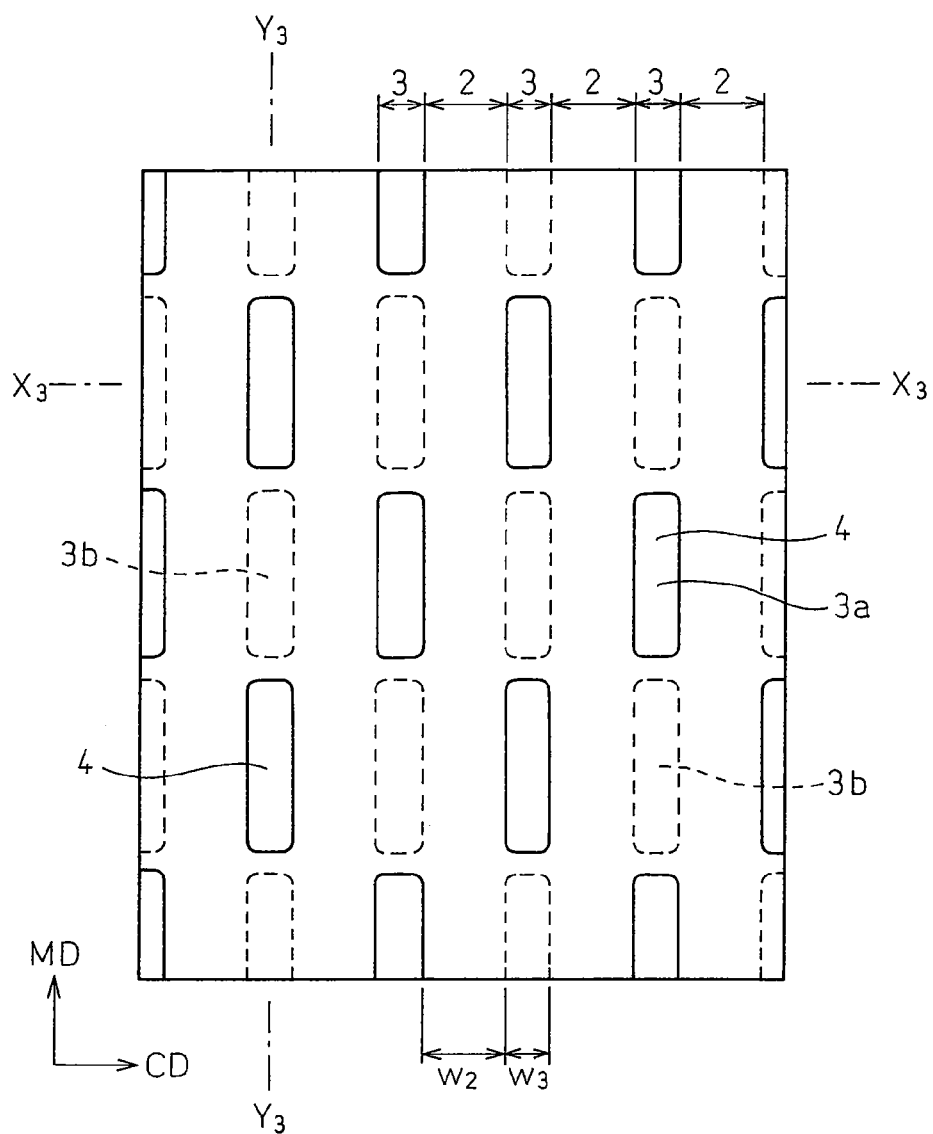
FIG. 6 is an enlarged schematic drawing of an overhead view of a second embodiment of the non-woven fabric sheet of the present invention.

FIG. 6 is an enlarged schematic drawing of an overhead view of a second embodiment of the non-woven fabric sheet of the present invention.

Figure 7:
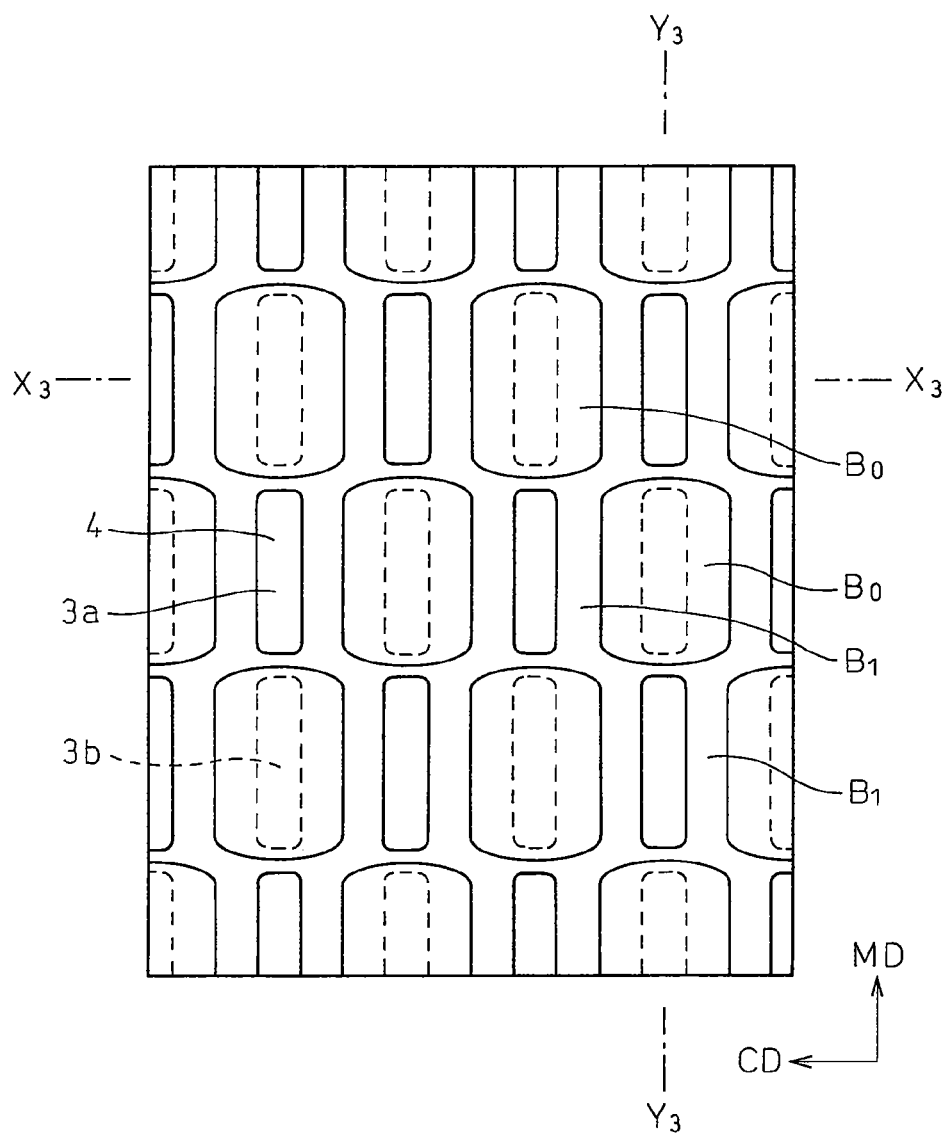
FIG. 7 is an enlarged schematic drawing of a bottom view of a second embodiment of the non-woven fabric sheet of the present invention.

FIG. 7 is an enlarged schematic drawing of a bottom view of a second embodiment of the non-woven sheet of the present invention.

Figure 8:
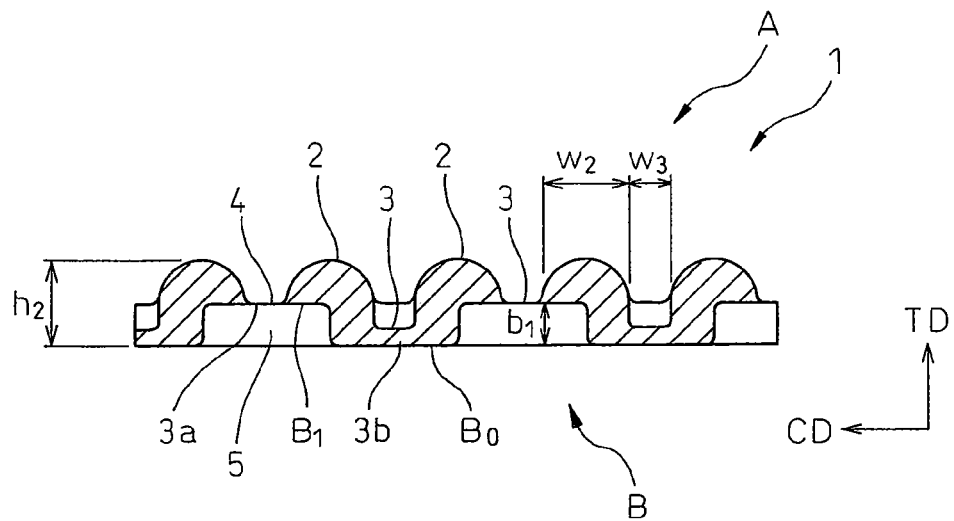
FIG. 8 is an enlarged schematic drawing of a cross-sectional view taken along line $X_3$-$X_3$ of FIG. 6.

FIG. 8 is an enlarged schematic drawing of a cross-sectional view taken along line $X_3$-$X_3$ of FIG. 6.

Figure 9:
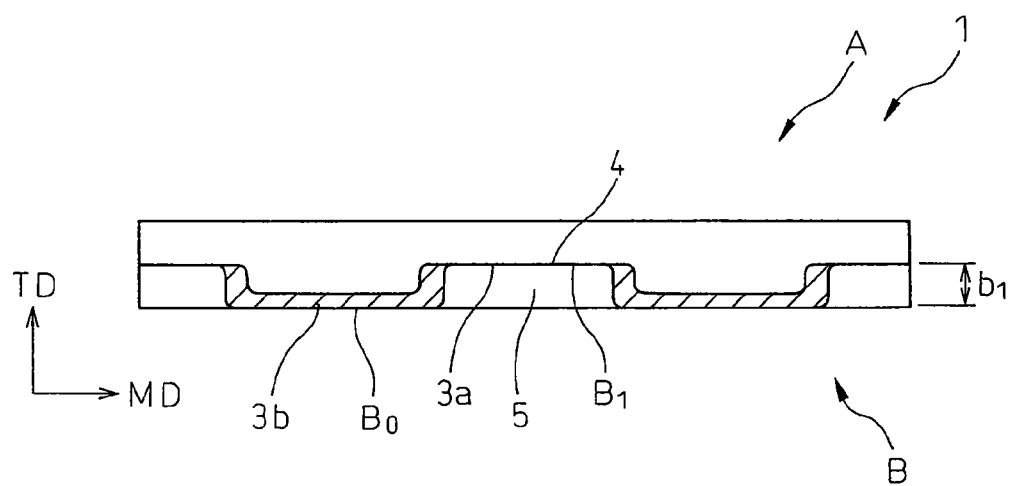
FIG. 9 is an enlarged schematic drawing of a cross-sectional view taken along line $Y_3$-$Y_3$ of FIG. 6.

FIG. 9 is an enlarged schematic drawing of a cross-sectional view taken along line $Y_3$-$Y_3$ of FIG. 6.

Figure 25:
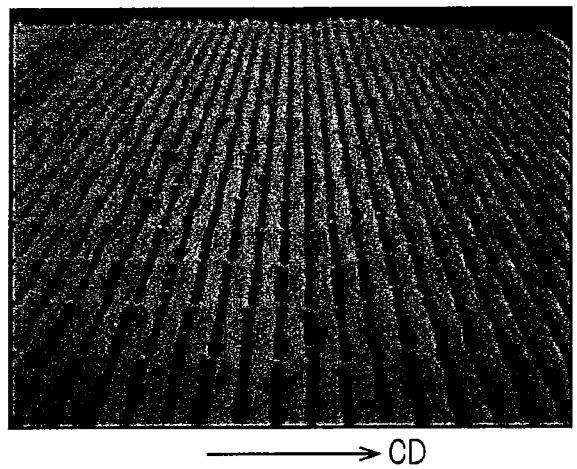
FIG. 25 is a perspective photograph taken from the longitudinal direction of the front surface of a non-woven fabric sheet obtained in Example 2.

FIG. 25 is a perspective photograph taken from the longitudinal direction of the front surface of a non-woven fabric sheet of a second embodiment.

Figure 26:
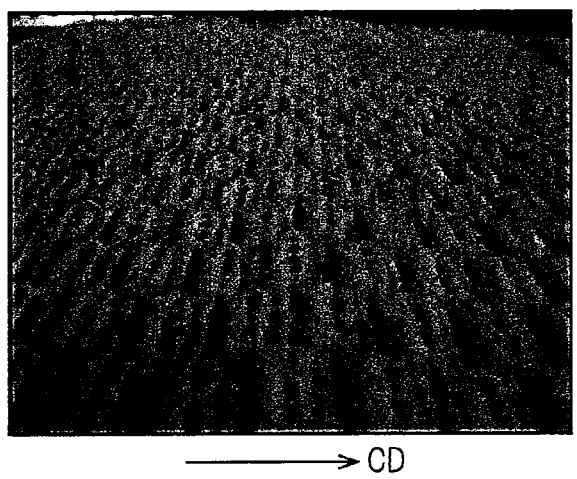
FIG. 26 is a perspective photograph taken from the longitudinal direction of the back surface of a non-woven fabric sheet obtained in Example 2.

FIG. 26 is a perspective photograph taken from the longitudinal direction of the back surface of a non-woven fabric sheet of a second embodiment.

The non-woven fabric sheet 1 has mutually perpendicular longitudinal, transverse and thickness directions, the front surface A and the back surface B on the opposite side thereof in the direction of thickness, and the ridges 2 and the grooves 3 alternatively formed in alternate rows in the front surface A so as to form repeated undulations in the transverse direction extending mutually in parallel in the longitudinal direction.

The non-woven fabric sheet 1 has the bottom surfaces $B_0$ that contact the aforementioned horizontal surface when the non-woven fabric sheet 1 is placed on the horizontal surface with the back surface B facing down. The back surface B has the bottom surfaces $B_0$ and the surfaces $B_1$ of a height $b_1$ from the horizontal surface. The sites 3a where the height from the bottom surfaces $B_0$ is relatively high and the sites 3b corresponding to the bottom surfaces $B_0$ are alternately formed in the longitudinal direction as shown in FIG. 3 on the back surface of the grooves 3. The openings 4 are at least formed in the sites 3a where the height from the bottom surfaces is relatively high, and the space 5 is provided below the openings 4. Furthermore, although openings are not necessarily required to be formed in the sites 3b corresponding to the bottom surfaces $B_0$, openings may be formed therein.

In the non-woven fabric sheet of the second embodiment, as shown in FIG. 7, the bottom surfaces $B_0$ and the surfaces $B_1$ are arranged in a staggered pattern, each bottom surface B0 is separated from the adjacent bottom surfaces $B_0$, and each surface $B_1$ is connected to four adjacent surfaces $B_1$. Namely, the space 5 is connected in a staggered pattern.

The height $b_1$ (location of the openings 4) from the bottom surfaces of the relatively high sites 3a of the back surface of the grooves 3 (see FIG. 9) is preferably 0.5 mm to 15 mm and more preferably 1 mm to 5 mm from the viewpoint of providing the space 5 for introducing highly viscous excrement liquid below the openings 4. In the case of exceeding these ranges, since the ridge height inevitably ends up becoming excessively high, product thickness when installed in a product becomes excessively thick and feeling of use when worn ends up increasing. In addition, in the case of being below these ranges, the retention volume formed below the openings 4 is inadequate.

A height $h_2$ (see FIG. 8) from the horizontal surface of the front surface on the front side of the ridges 2 is preferably 0.8 mm to 20 mm and more preferably 1.2 mm to 7 mm from the viewpoints of reducing rewetting of highly viscous liquid in the non-woven fabric sheet 1 and feeling of use when worn. In the case of exceeding these ranges, product thickness becomes excessively thick when installing in a product, and the feeling of use when worn ends up increasing. In addition, in the case of being below these ranges, re-adherence to the skin cannot be reduced since the highly viscous liquid is not adequately separated from the skin.

In addition, the width $w_2$ of the ridges 2 in the transverse direction of the non-woven fabric 1 is preferably 1 to 10 mm and more preferably 2 mm to 5 mm from the viewpoints of separating highly viscous liquid from the skin and moldability. In the case of exceeding these ranges, highly viscous liquid remains at a location close to the skin since regions where highly viscous liquid adhere to the ridges increases, thereby preventing re-adherence to the skin from being reduced. In addition, in the case of being below these ranges, molding of the irregular surface structure ends up becoming difficult.

The width $w_3$ in the transverse direction of the non-woven fabric sheet 1 is preferably 0.5 mm to 7 mm and more preferably 1 mm to 3 mm from the viewpoints of introducing a highly viscous liquid through openings formed in the grooves and separating highly viscous liquid from the skin. In the case of exceeding these ranges, there is increased susceptibility of the base material arranged on the skin and upper layer side digging into the grooves 3, and since regions where highly viscous liquid is separated from the skin become smaller as a result thereof, re-adherence to the skin cannot be reduced. In addition, in the case of being below these ranges, it ends up becoming difficult to introduce highly viscous liquid into the space below the openings.

Fibers composed of a thermoplastic polymer material are preferably used for the fibers that compose the non-woven fabric sheet. Examples of thermoplastic polymer materials include polyolefins such as polyethylene or polypropylene, polyesters such as polyethylene terephthalate, and polyamides. In addition, core-sheath or side-by-side type composite fibers consisting of a combination of these thermoplastic polymer materials can also be used. The fibers are preferably fibers in which intersections of the fibers can be heat-fused, and examples thereof include composite fibers of a low melting point resin and a high melting point resin. In addition, in the case of using the non-woven fabric sheet 1 as a top sheet of an absorbent article, the fineness of the fibers used is preferably 1 dtex to 5 dtex and more preferably 2.6 dtex to 3.3 dtex from the viewpoints of feel on the skin and absorbency. In addition, the length of the fibers used is preferably 15 mm to 65 mm and more preferably 38 mm to 51 mm from the viewpoint of proper carding. In the case of using the non-woven fabric sheet 1 as a member other than the top sheet of an absorbent article, such as in the case of using as a second sheet or arranging in a portion that passes through an absorbent body, thicker fibers (such as those having fineness of 5 dtex to 12 dtex) can be used.

In addition, the fibers that compose the non-woven fabric sheet may be composed of two or more types of fibers in which the intersections thereof can be heat-fused, or may be composed by containing fibers in which the intersections thereof can be heat-fused and other fibers that are not heat-fused with those fibers. For example, one or more types of fibers can be arbitrarily selected and used from among regenerated fibers such as rayon fibers, semi-synthetic fibers such as acetate fibers, natural fibers such as cotton or wool fibers, and synthetic fibers such as polypropylene, polyethylene, polyester, nylon, polyvinyl chloride or vinylon fibers.

In addition, there are no limitations on the cross-sectional shape and so forth of the fibers used, and split-type composite fibers or modified cross-section fibers can be used arbitrarily. In this case, the amount of fibers for which intersections thereof can be heat-fused is preferably 60% by weight to 95% by weight and more preferably 70% by weight to 90% by weight of the non-woven fabric sheet.

In addition, the non-woven fabric sheet may be composed of a single layer of two or more fibrous layers. In the case of the latter, the layers are integrated into a single unit by a method such as fiber entanglement or heat fusion at the surface where both are opposed. In the case of being composed of two fibrous layers, although the fiber fineness of the upper layer is preferably 1 dtex to 5 dtex, fibers of greater thickness (such as those having a fineness of 5 dtex to 12 dtex) can be used for the fibers of the lower layer.

The non-woven fabric sheet 1 is preferably hydrophilic. The non-woven fabric sheet 1 can be made to be hydrophilic by, for example, using fibers that have been treated with a hydrophilizing agent for the raw material thereof. In addition, a method can also be used in which fibers incorporating a hydrophilizing agent are used for the raw material. Moreover, a method can also be used that uses fibers inherently possessing hydrophilicity, such as natural fibers or semi-natural fibers. The non-woven fabric sheet 1 can also be made to be hydrophilic following the manufacturing thereof by coating with a surfactant.

Next, an explanation is provided of a method for manufacturing the non-woven fabric sheet of the present invention.

The manufacturing method of the present invention comprises the following steps:

a) a step for obtaining a web by opening a fiber assembly by passing through a carding machine, b) a step for placing the web obtained in step a) on a pattern plate, on which convex portions having a comparatively large air flow resistance and concave portions having a comparatively small air flow resistance are arranged in a regular pattern, and spraying a fluid onto the web from a plurality of nozzles arranged in a row in the cross-machine direction while transporting over the pattern plate, and c) a step for heating the web and fusing at sites where fibers are mutually intersecting.

Figure 10:
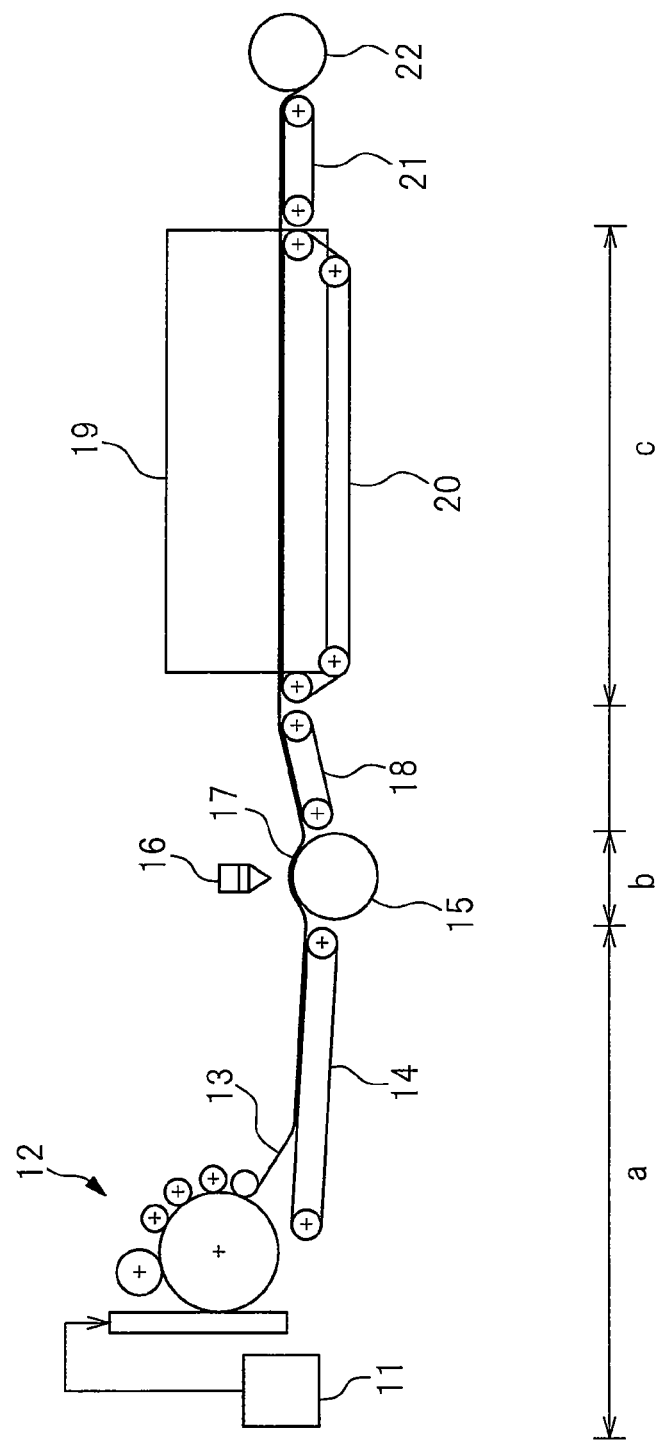
FIG. 10 is a drawing showing an example of a manufacturing process of the non-woven fabric sheet of the present invention.

FIG. 10 is a drawing showing an example of a manufacturing process of the non-woven fabric sheet of the present invention. However, the present invention is not limited to this example.

In FIG. 10, reference symbol a indicates step a, reference symbol b indicates step b, and reference symbol c indicates step c.

In step a, a fiber assembly is transported from a container 11 to a carding machine 12, and the fiber assembly is opened by passing through the carding machine to form a web 13. The formed web 13 is then transported by being placed on an endless belt 14.

Step b is a step for placing the web obtained in step a on a pattern plate, on which convex portions having a comparatively large air flow resistance and concave portions having a comparatively small air flow resistance are arranged in a regular pattern, and spraying a fluid onto the web from a plurality of nozzles arranged in a row in the cross-machine direction while transporting over the pattern plate.

The machine direction refers to the direction in which the web is transported in the manufacturing process, while the cross-machine direction refers to the direction perpendicular to the machine direction in the web plane. In the following descriptions, the machine direction is referred to as MD, while the cross-machine direction is referred to as CD.

Step b in FIG. 10 includes a suction drum 15 that rotates in the machine direction MD, and a plurality of nozzles 16 arranged in a row in the cross-machine direction CD. The plurality of nozzles 16 arranged in a row in the cross-machine direction are able to spray a fluid towards the circumferential surface of the suction drum 15, and are separated from the circumferential surface of the suction drum 15 by a required dimension. The plurality of nozzles 16 arranged in a row in the cross-machine direction are attached at prescribed intervals to a pipe (not shown) extending in the axial direction of the suction drum 15, namely the cross-machine direction CD.

Although the plurality of nozzles 16 arranged in a row in the cross-machine direction may consist of a single row as shown in FIG. 11(*a*), the nozzles are preferably composed by arranging in two or more rows from the viewpoint of fiber penetrability. For example, the nozzles may be composed of nozzle rows 16*a*, 16*b* and 16*c* as shown in FIG. 11(*b*), and in a preferable example of an attached state thereof, the nozzles 16 are adjusted so as to be located along the same line in the machine direction MD in each of the nozzle rows 16*a*, 16*b* and 16*c*. In addition, the nozzle rows 16*a*, 16*b* and 16*c* can be arranged while separated by intervals of 30° each, for example, in the circumferential direction of the suction drum 15 as shown in FIG. 12, and the nozzles 16 of each of the nozzle rows 16*a*, 16*b* and 16*c* can be attached to a pipe at a pitch P of 5 mm, for example, in the cross-machine direction. Fluid of a prescribed temperature can be sprayed at a prescribed air blowing rate from the nozzle rows 16*a*, 16*b* and 16*c*. The fluid sprayed from the plurality of nozzles 16 is adjusted so as not to disturb the distribution state of the fibers in the web as a result of mutual interference between the fluid per se or fluid from the nozzles 16. In order to accomplish this, in the case, for example, a web having a basis weight of 35 g/m$^2$ passes over the circumferential surface of the suction drum 15 having a diameter of 500 mm in 0.5 seconds, the nozzles 16 of each of the nozzle rows 16*a*, 16*b* and 16*c* are arranged at a pitch P of 5 mm in the cross-machine direction, the distance from the circumferential surface of the suction drum 15 is adjusted to 5 mm to 8 mm, and the web 13 preferably passes beneath the plurality of nozzles 16 arranged in a row in the cross-machine direction after adjusting the thickness to about 2 mm to 5 mm with the suction of the suction drum 15. The aperture of the nozzles 16 used at this time is preferably about 0.5 mm to 1.5 mm, the spraying rate of fluid from the nozzles 16 is preferably 50 m/sec to 700 m/sec, and the suctioning force of the suction drum 15 is preferably an air blowing rate of 2 m/sec to 7 m/sec.

The pattern plate is attached to the circumferential surface of the suction drum 15. The pattern plate has convex portions having comparatively large air flow resistance and concave portions having comparatively small air flow resistance arranged in a regular pattern. The combination of convex portions having comparatively large air flow resistance and concave portions having comparatively small air flow resistance may be a combination of convex portions not allowing the passage of fluid and concave portions allowing the passage of fluid.

Figure 13:
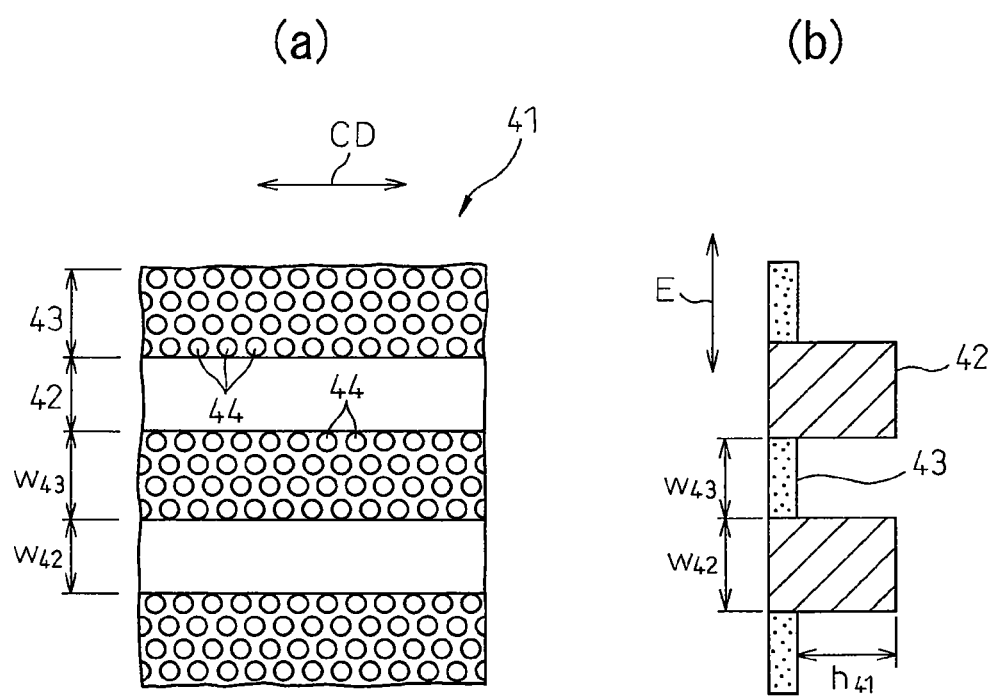
FIG. 13 is a drawing showing an example of a pattern plate.

An example of the pattern plate is shown in FIG. 13. FIG. 13(*a*) is an overhead view of a pattern plate 41, while FIG. 13(B) is a cross-sectional view taken along the circumferential direction E of the pattern plate 41 (machine direction MD). This pattern plate has convex portions 42 and concave portions 43, extending in parallel in the cross-machine direction CD and alternately formed in the circumferential direction E of the suction drum 15 on the circumferential surface thereof, a large number of holes 44 are formed in the concave portions 43, and the holes 44 are connected to a suction mechanism (not shown) of the suction drum 15. Use of the pattern plate shown in FIG. 13 enables the fabrication of a non-woven fabric sheet of the aforementioned first embodiment.

In one example of the pattern plate 41, a height difference $h_{41}$ between the concave and convex portions of the pattern plate is 1 mm to 20 mm. A width $w_{43}$ in the circumferential direction E of the concave portions 43 of the pattern plate is 2 mm to 3 mm, the concave portions 43 of the pattern plate extend nearly over the entire direction of width of the suction drum 15, namely in the cross-machine direction CD, and a large number of holes 44 having a diameter of 0.2 mm to 1 mm are formed at an aperture ratio of 15% to 30% with respect to the surface area of the concave portions 43 of the pattern plate. A width $w_{42}$ in the circumferential direction of the convex portions 42 of the pattern plate is 1.5 mm to 3 mm, and the convex portions 42 extend over the entire direction of width of the suction drum 15, namely in the cross-machine direction CD.

Another example of the pattern plate is shown in FIG. 14. FIG. 14(*a*) is an overhead view of the pattern plate 41, while FIG. 14(*b*) is a cross-sectional view taken along the direction of width (cross-machine direction CD) of the pattern plate 41 (cross-sectional view taken along line $X_4$-$X_4$ of FIG. 14(*a*)). In this pattern plate, hexagonally shaped concave portions 43 are arranged in a scattered pattern. The concave portions 43 are fabricated with a material such as a metal mesh that allows the passage of fluid (member having comparatively small air flow resistance), and are connected to a suction mechanism (not shown) of the suction drum 15. The convex portions 42 that do not allow the passage of fluid (having comparatively large air flow resistance) constitute portions other than the concave portions 43, and each of the convex portions 42 is connected to four adjacent convex portions 42. When the circumferential surface of the suction drum 15 is fabricated with a member such as a metal mesh that allows the passage of a fluid, the circumferential surface of the suction drum 15 may also serve as a member 45 that composes the concave portions 43. Use of the pattern plate shown in FIG. 14 enables the fabrication of a non-woven fabric sheet of the aforementioned second embodiment. When using the pattern plate shown in FIG. 14, the nozzles are preferably arranged on a line that passes through the centers of the hexagons arranged in the machine direction MD.

Although hexagonal concave portions 43 are shown in FIG. 14, there are no limitations on the shape of the concave portions 43, and they may be of any shape. For example, squares, rectangles, rhomboids, polygons, circles or ovals can be employed. The shape of the concave portions 43 determines the shape of the bottom surfaces $B_0$ of the non-woven fabric sheet of the aforementioned second embodiment.

Typical examples of the dimensions of each portion of the pattern plate shown in FIG. 14 consist of $d_1=d_2=d_3=4$ mm, $d_4=8$ mm, $d_5=11$ mm, $d_6=d_7=9$ mm, $d_8=d_9=10$ mm, and $d_{10}=20$ mm. However, the present invention is not limited to these dimensions. A height difference between the concave and convex portions of the pattern plate (depth of concave portions) $d_{11}$ is preferably 0.5 mm to 20 mm and more preferably 1 mm to 5 mm. The depth $d_{11}$ of the concave portions is equivalent to the height $b_1$ of the surfaces $B_1$ of the resulting non-woven fabric sheet.

The peripheral velocity of the suction drum 15 to which the pattern plate 41 is attached is the same as the transport speed of the web.

In step b, the web 13 is then placed on the circumferential surface of the suction drum 15 and passes beneath the nozzles 16. Although a fluid is sprayed towards the web 13 from the nozzles 16, in the suction drum 15, the suction acts to suction the fluid. In the web 13 that has been sprayed with fluid, fibers directly beneath the nozzles 16 move in parallel in the cross-machine direction and accumulate between the adjacent nozzles 16 to form the ridges 2. On the other hand, the grooves 3 are formed directly beneath the nozzles 16. At this time, since the web 13 is arranged on the surface irregularities of the pattern plate, the fibrous layer directly beneath the nozzles is pushed into the shape of the surface irregularities, and the sites 3*a* where the height from the bottom surfaces is relatively high and the sites 3*b* corresponding to the bottom surfaces are alternately arranged in the longitudinal direction on the grooves 3 formed.

Moreover, fluid sprayed towards the web 13 flows in the cross-machine direction CD along the surface of the pattern plate 41 without penetrating inside the suction drum 15 at the convex portions 42 of the pattern plate 41 that composes the circumferential surface of the suction drum 15. The openings 4 are formed in the web 13 when nearly all of the fibers placed on the convex portions 42 have been moved in the cross-machine direction CD by this fluid. In addition, when the majority of the fluid sprayed towards the fibers placed on the concave portions 43 of the pattern plate 41 has penetrated inside the suction drum 15 by passing through the holes 44 in the pattern plate 41, although a portion of those fibers move in the cross-machine direction CD, the majority remain in place and form bridges connecting adjacent ridges 2. At this time, the openings 4 are formed to a height intermediate to the apex height $h_{2a}$ (or $h_2$) of the ridges and bottom surfaces $B_0$, and the space 5 is formed below the openings 4.

In addition, in the case of increasing the air flow resistance in the concave portions 43, or in the case of increasing the amount of fluid flowing in the cross-machine direction CD along the surface of the pattern plate 41 as a result of increasing the air blowing rate at which the fluid is sprayed, fibers easily move in the cross-machine direction CD even when directly beneath the nozzles 16, and as a result of fibers directly beneath the nozzles 16 moving in parallel in the cross-machine direction CD and accumulating between adjacent nozzles 16, sites where basis weight is relatively high and sites where basis weight is relatively low are formed.

The fluid sprayed from the nozzles 16 may be a gas such as air or steam or may be a liquid such as water. In addition, the fluid may also be an aerosol containing a solid or fine particles in a gas.

A web 17 in which fibers have been rearranged is placed on an endless conveyor 18 and is transported to step c.

Step c is a step for heating the web 17, in which ridges and grooves have been formed, and fusing at sites where fibers are mutually intersecting. A heat treatment dryer 19 is provided in step c, and the web 17 is placed on an endless belt 20 and passed through the heat treatment dryer 19 to carry out heat treatment therein. In step c, heat treatment is carried out at a temperature equal to or higher than the fusion starting temperature of the fibers, and the shape of the surface irregularities formed in step b is fixed by fusing the fibers at those sites where they mutually intersect.

The temperature of the heat treatment dryer 19 is preferably −10° C. to +40° C. higher than the melting point of the fibers and more preferably 0° C. to +20° C. higher than the melting point of the fibers. For example, in the case the melting point of the fibers is 130° C., the temperature of the heat treatment dryer 19 is preferably 120° C. to 170° C. and more preferably 130° C. to 150° C. In the case the fiber assembly contains composite fibers of a low melting point resin and high melting point resin, the temperature of the heat treatment dryer 19 is preferably equal to or higher than the fusion starting temperature of the low melting point resin and lower than the melting starting temperature of the high melting point resin.

The web that has come out of the heat treatment dryer 19 is placed on an endless belt 21 and cooled at room temperature while being transported. As a result of cooling, fusion at those sites where the fibers mutually intersect is fixed resulting in fixation of the surface irregularities of the non-woven fabric sheet. The cooled web is then wound onto a roller 22.

The non-woven fabric sheet of the present invention can be preferably used in an absorbent article such as a disposable diaper. For example, in addition to being able to be used as a top sheet or second sheet of an absorbent article, the non-woven fabric sheet can also be arranged on a side closer to the upper side than a back sheet such as by arranging in a portion that passes through an absorbent body. The non-woven fabric sheet can be used particularly preferably as a top sheet of a disposable diaper. Furthermore, when installing the non-woven fabric sheet of the present invention in an absorbent article, the non-woven fabric sheet may be arranged by aligning the direction in which the ridges 2 and grooves 3 of the non-woven fabric sheet extend (longitudinal direction) with either the lengthwise direction, widthwise direction or diagonal direction of the absorbent article.

Since openings are formed at regions located at an intermediate height of the ridges, the non-woven fabric sheet of the present is able to increase the volume of highly viscous excrement liquid introduced below the openings. In cases in which openings are formed in a bottom surface, since contact area increases at the interface between the bottom and a base material arranged there below, the openings are substantially covered, and a highly viscous liquid such as soft stool cannot be expected to permeate by using the openings. In addition, in cases in which openings are present near the apex of ridge height, since a base material arranged on the skin or on the non-woven fabric sheet of the present invention is in contact with the openings, there is no space for absorbing highly viscous liquid that has flowed back through the openings during rewetting, and diffusion of the highly viscous liquid is presumed to increase at this location of contact.

In addition, since openings are formed at regions located at an intermediate height of the ridges, regions of contact between the skin and non-woven fabric sheet can be reduced due to the shape of the irregular surface above the openings.

Moreover, as a result of at least a portion of the space formed below the openings being connected to the space formed below adjacent openings, a flow path is formed that allows excrement liquid that has been introduced through the openings to move over the back surface of the sheet.

Thus, when the non-woven fabric sheet of the present invention is used as a top sheet of a disposable diaper, for example, the range over which a watery stool produced by newborn infants diffuses on the front side can be decreased and the amount that re-adheres to the skin can be reduced.

The third subject invention is an absorbent article that uses the non-woven fabric sheet of the first subject invention. Examples of absorbent articles include paper diapers and sanitary napkins. The absorbent article of the present invention is able to decrease the range of watery stool produced by newborn infants that diffuses on the front side thereof, as well as reduce the amount that re-adheres to the skin.

EXAMPLES

Example 1

A non-woven fabric sheet was manufactured using the manufacturing device shown in FIG. 10.

In step a, core-sheath type composite fibers (core: polyethylene terephthalate, sheath: polyethylene, thickness: 3.3 dtex, fiber length: 51 mm, core:sheath weight ratio: 50/50) were used as fibers of a fiber assembly, and a web was formed having a basis weight of 35 g/m$^2$.

In step b, the web was sprayed at a flow rate of 125 m/s using the pattern plate shown in FIG. 13 (dimension $w_{42}$ in circumferential direction of convex portions not allowing the passage of fluid=2.3 mm, dimension $w_{43}$ in the circumferential direction of concave portions allowing the passage of fluid=2.7 mm, diameter of holes 44 of concave portions=0.8 mm (45° scattered pattern), aperture ratio of concave portions=22%, height difference $h_{41}$ between concave portions and convex portions=3.0 mm), using one row of nozzles having an aperture of 1.0 mm and pitch of 4 mm, and using air at about 160° C. for the sprayed fluid. The distance between the nozzles and the suction drum was set at 5.0 mm, and the suctioning force of the suction drum was set to an air blowing rate of 5 m/s.

In step c, heat treatment was carried out for 10 seconds at about 138° C. and an air blowing rate of 0.7 m/s.

Photographs of the resulting non-woven fabric sheet are shown in FIGS. 15 to 20.

FIG. 15 depicts photographs of the front surface of the non-woven fabric sheet of Example 1 (taken with a digital camera), FIG. 15(*a*) is a perspective image as viewed from the longitudinal direction, and FIG. 15(*b*) is a perspective image as viewed from the transverse direction.

FIG. 16 depicts photographs of the back surface of the non-woven fabric sheet of Example 1 (taken with a digital camera), FIG. 16(*a*) is a perspective image as viewed from the longitudinal direction, and FIG. 16(*b*) is a perspective image as viewed from the transverse direction.

FIG. 17 is a photograph of an enlarged perspective view of the essential portion of the non-woven fabric sheet of Example 1.

FIG. 18 is a photograph of a cross-section taken along line $Y_4$-$Y_4$ of FIG. 17 (sectioned along the longitudinal direction of the grooves 3).

FIG. 19 is a photograph of a cross-section taken along line $X_5$-$X_5$ of FIG. 17 (sectioned along the transverse direction of the sites 3b corresponding to the bottom surfaces $B_0$.

FIG. 20 is a photograph of a cross-section taken along line $X_6$-$X_6$ of FIG. 17 (sectioned along the transverse direction and passing through the apices of the ridges 2).

Example 2

Figure 21:
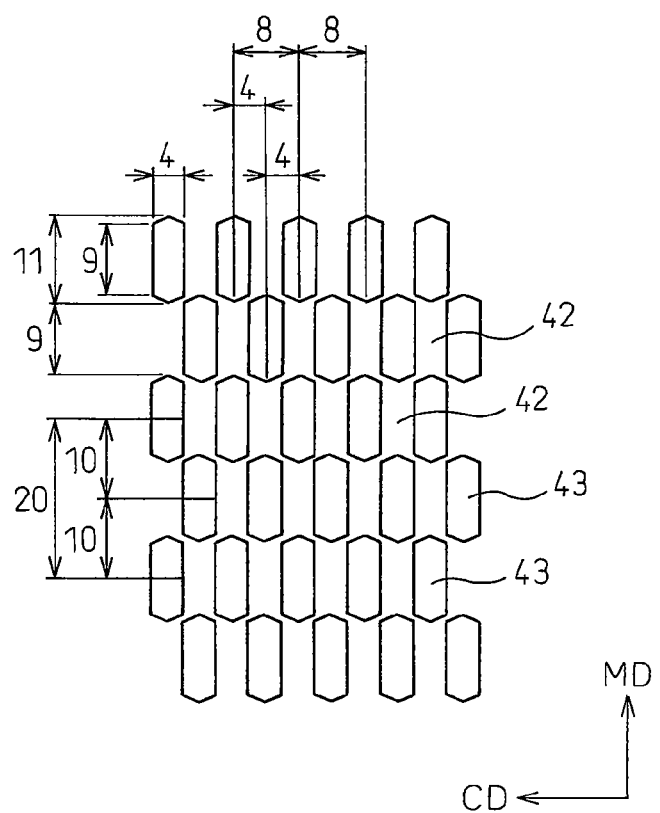
FIG. 21 is an overhead view of a pattern plate used in Example 2.

A non-woven fabric sheet was manufactured in the same manner as Example 1 with the exception of changing the pattern plate to that shown in FIG. 21 (dimensions in the drawing are in mm units), not providing the pattern plate with the member 45 for allowing the passage of fluid, changing the thickness d11 of the pattern plate to 1 mm, and attaching the pattern plate to the circumferential surface of the suction drum 15 fabricated with a metal mesh that allows the passage of fluid.

Figure 22:
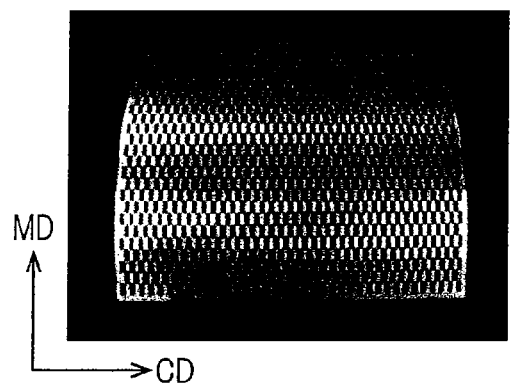
FIG. 22 is a photograph of a pattern plate used in Example 2.
Figure 23:
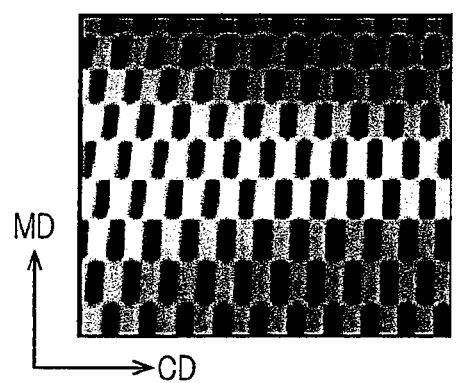
FIG. 23 is an enlarged photograph of a pattern plate used in Example 2.
Figure 24:
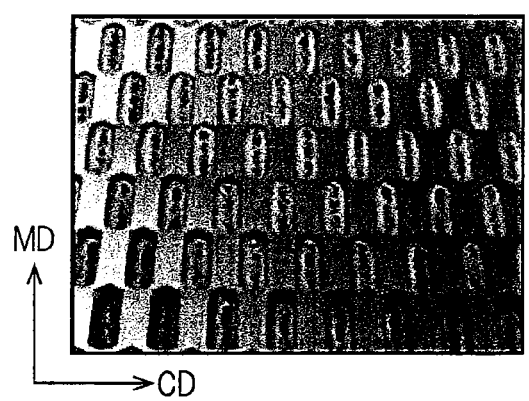
FIG. 24 is a photograph of the back surface of a pattern plate used in Example 2 during the manufacturing process.

A photograph of the pattern plate used is shown in FIG. 22, an enlarged photograph thereof is shown in FIG. 23, and an image of the back side during the manufacturing process is shown in FIG. 24.

Photographs of the resulting non-woven fabric sheet are shown in FIGS. 25 and 26.

FIG. 25 is a perspective photograph taken from the longitudinal direction of the front surface of the non-woven fabric sheet of Example 2 (taken with a digital camera).

FIG. 26 is a perspective photograph taken from the longitudinal direction of the back surface of the non-woven fabric sheet of Example 2 (taken with a digital camera).

Comparative Example 1

A non-woven fabric sheet was manufactured in the same manner as Example 1 with the exception of changing the pattern plate to that having the same shape as that shown in FIG. 13 except for being flat ($h_{41}$=0 mm).

Comparative Example 2

A non-woven fabric sheet was manufactured in the same manner as Example 1 with the exception of not carrying out step b and changing the basis weight of the web formed in step a to 25 g/m².

Diffusion area, re-adherence rate and permeability were measured for the non-woven fabric sheet obtained in the examples and comparative examples.

Figure 27:
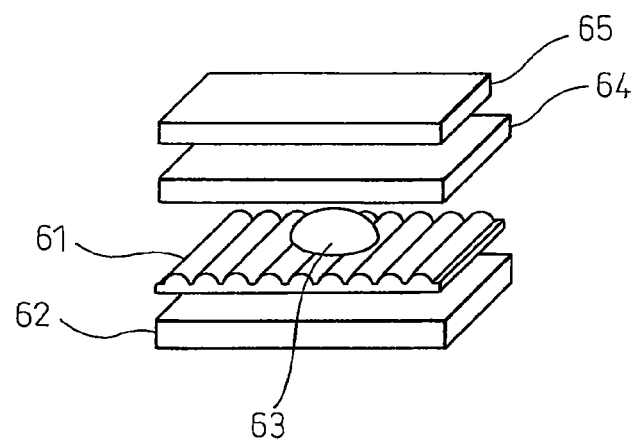
FIG. 27 is a drawing for explaining a method for measuring diffusion area and other parameters.

Furthermore, diffusion area, re-adherence rate and permeability were measured as described below (see FIG. 27).

(1) A sample of each non-woven fabric sheet was cut out to a size of 100 mm×100 mm.

(2) Approximately 30 of a sample 61 was arranged on of filter paper 62 (Advantec Co., Ltd., size: 100 mm×100 mm, type: Ananashi, quantity: 100).

(3) 5.0 g of artificial soft stool 63 were dropped onto the surface of the sample 61 at a rate of about 1 g/s. Furthermore, a mixture of bentonite (Ben-Gel, Hojun Co., Ltd.), powdered cellulose (KC Flock Grade W-200, Nippon Paper Industries, Chemical Div.) and ion exchange water mixed at a ratio of 3:6.7:90 to which a dye (red dye no. 5) was further added was used for the artificial soft stool.

(4) After 60 seconds, 30 g of filter paper 64 and a 70 g weight 65 were placed on the sample to subject to a load of 1 g/cm² for 30 seconds.

(5) After removing the weight 65, the weight of artificial soft stool that transferred to the filter paper 64 was measured from the difference in weight before and after measurement as the re-adhered amount (g). The re-adherence rate was then calculated using the following formula.

Re-adherence rate (%)=(re-adhered amount/5.0)×100

(6) Next, the sample 61 was removed, and the weight of artificial soft stool that permeated the sample 61 was measured as the permeated amount (g) from the weights of the filter paper arranged below before and after measurement. Permeability was then calculated using the following formula.

Permeability (%)=(permeated amount/5.0)×100

(7) Following this series of measurements, photographs were taken of the filter paper 64 to which the artificial soft stool re-adhered, and the filter paper 62 arranged below containing the permeated artificial soft stool.

(8) Images incorporated with a scanner were then processed using image analysis software in the form of USB Digital Scale (Scalar Corp.) to determine diffusion area.

The procedure for processing images with the USB Digital Scale image analysis software used when determining diffusion area is as described below.

(1) An image of the side of the non-woven fabric sheet that faces the skin when worn was incorporated with a scanner while placing a white mount on the back.

(2) USB Digital Scale image analysis software (Scalar Corp.) was started up followed by loading the image acquired in (1).

(3) After having set binarization to 0 to 150, the scanned image was converted by static binarization.

(4) The range of the sample size was specified (100 mm×100 mm).

(5) The shape characteristic extraction command was selected, black was selected for the target color in the count tab, the width and height of the extraction target was specified to 0 pixels or more, and the count button was pressed to extract the portion where the artificial soft stool had adhered.

(6) Continuing, total area was specified with the extracted volume tab, and the feature value button was pressed to allow measurement of the area of the portion where the artificial soft stool had adhered (black portion).

(7) Diffusion area was calculated using the following formula.

Figure 28:
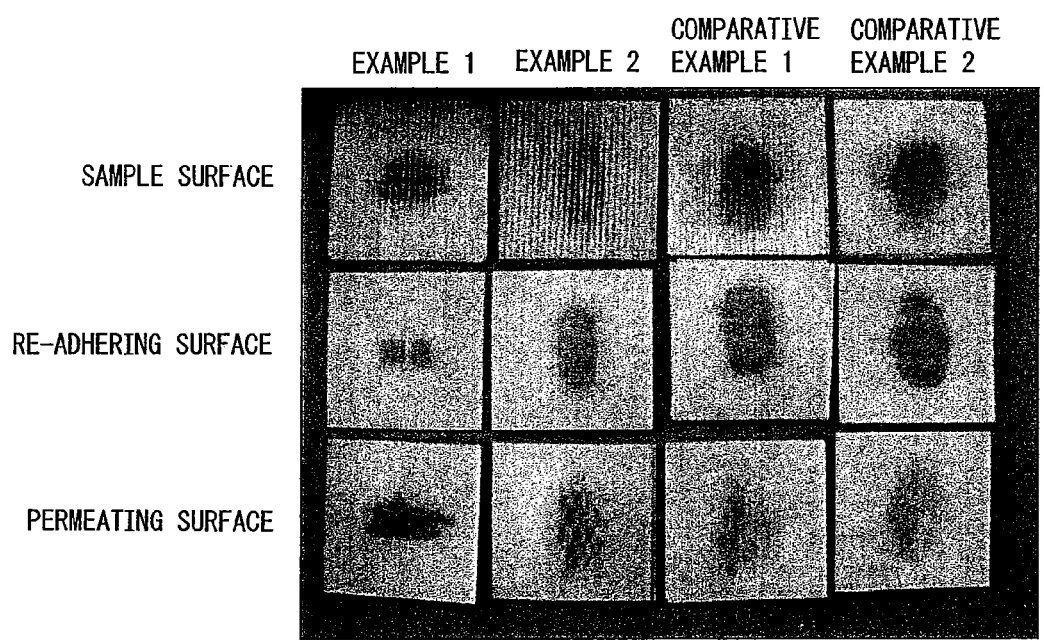
FIG. 28 shows images of sample surfaces, re-adhering surfaces and permeating surfaces when measuring diffusion area and other parameters of non-woven fabric sheets of examples and comparative examples.

Diffusion area=area of portion where artificial soft stool re-adhered within measuring range (black portion)/area of specified range Images of the sample surfaces, re-adhering surfaces and permeating surfaces photographed for Examples 1 and 2 and Comparative Examples 1 and 2 are shown in FIG. 28.

Figure 29:
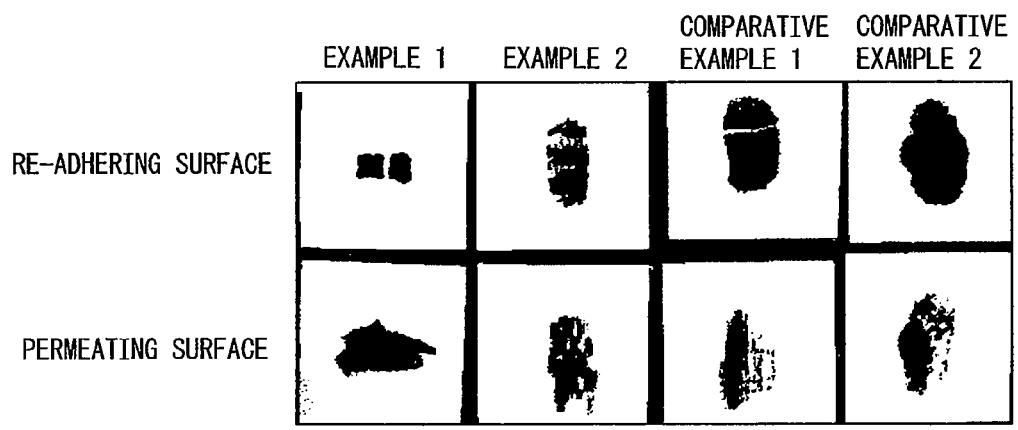
FIG. 29 shows binarized images of the re-adhering surfaces and permeating surfaces of FIG. 28 obtained with image analysis software.

FIG. 29 shows binarized images of the re-adhering surfaces and permeating surfaces of the images shown in FIG. 28.

The calculated values for diffusion area, re-adherence rate and permeability are shown in Table 1.

TABLE 1

|  |  | Ex. 1 | Ex. 2 | Comp. Ex. 1 | Comp. Ex. 2 |
|---|---|---|---|---|---|
| Diffusion area (cm²) | Front | 4.2 | 9.2 | 14.8 | 17.8 |
|  | Back | 11.6 | 10.9 | 8.7 | 10.2 |

TABLE 1-continued

|  | Ex. 1 | Ex. 2 | Comp. Ex. 1 | Comp. Ex. 2 |
|---|---|---|---|---|
| Re-adherence rate (%) | 10 | 23 | 55 | 41 |
| Permeability (%) | 35 | 26 | 15 | 20 |

As can be understood from Table 1, the non-woven fabric sheet of the present invention demonstrated a smaller front surface diffusion area, larger back surface diffusion area, lower re-adherence rate (rate of rewetting of the skin of upper base material) and higher permeability.

INDUSTRIAL APPLICABILITY

The non-woven fabric sheet of the present invention can be preferably used in an absorbent article such as a disposable diaper.

BRIEF DESCRIPTION OF THE REFERENCE SYMBOLS

1 Non-woven fabric sheet
2 Ridges
3 Grooves
3a Sites where height from bottom surfaces of back surfaces of grooves is relatively high
3b Sites corresponding to bottom surfaces of grooves
4 Openings
5 Space
11 Container
12 Carding machine
13 Web
14 Endless belt
15 Suction drum
16 Nozzles
17 Web
18 Endless belt
19 Heat treatment dryer
20 Endless belt
21 Endless belt
22 Roller
41 Pattern plate
42 Convex portions having comparative large air flow resistance
43 Concave portions having comparatively small air flow resistance
44 Holes
45 Member allowing passage of fluid

The invention claimed is:

1. A non-woven fabric sheet having mutually perpendicular longitudinal, transverse and thickness directions, having a front surface and an opposing surface thereto in the form of a back surface in the direction of thickness, and having ridges and grooves alternately formed so as to extend mutually in parallel in the longitudinal direction so as to form repeated undulations in the transverse direction; wherein, the non-woven fabric sheet has a bottom surface that contacts a horizontal surface when placed on the horizontal surface with the back surface, which is the opposing surface of the front surface that contacts the skin of a wearer, facing down, sites where the height from the bottom surface is relatively high and low sites corresponding to the bottom surface are alternately formed along the longitudinal direction on the back surface of the grooves, openings are formed at least in the sites where the height from the bottom surface is relatively high, and a space is provided below the openings,
wherein the portion corresponding to the bottom surface has a site having a relatively high basis weight and a site having a relatively low basis weight.

2. The non-woven fabric sheet according to claim 1, wherein the space provided below the openings is at least partially connected with a space provided below an adjacent opening.

3. The non-woven fabric sheet according to claim 2, wherein the back surface of the non-woven fabric sheet has a bottom surface $B_0$ and surface $B_1$ of a height $b_1$ from the bottom surface, the bottom surface $B_0$ extends in a transverse direction perpendicular to the longitudinal direction and each bottom surface $B_0$ is arranged in parallel, and the space is connected in the transverse direction perpendicular to the longitudinal direction.

4. The non-woven fabric sheet according to claim 3, wherein sites where the height from the bottom surface is relatively high and relatively low sites are alternately formed along the longitudinal direction on the front surface of the ridges, a space is present below the relatively high sites of the ridges, and the height of the space from the bottom surface is $b_1$.

5. The non-woven fabric sheet according to claim 2, wherein the back surface of the non-woven fabric sheet has a bottom surface $B_0$ and a surface $B_1$ of a height $b_1$ from the bottom surface, the bottom surface $B_0$ and the surface $B_1$ are arranged in a staggered pattern, each bottom surface $B_0$ is separated from the adjacent bottom surface $B_0$, and each surface $B_1$ is connected to four adjacent surfaces $B_1$.

6. The non-woven fabric sheet according to claim 1, wherein the back surface of the non-woven fabric sheet has a bottom surface $B_0$ and surface $B_1$ of a height $b_1$ from the bottom surface, the bottom surface $B_0$ extends in a transverse direction perpendicular to the longitudinal direction and each bottom surface $B_0$ is arranged in parallel, and the space is connected in the transverse direction perpendicular to the longitudinal direction.

7. The non-woven fabric sheet according to claim 6, wherein sites where the height from the bottom surface is relatively high and relatively low sites are alternately formed along the longitudinal direction on the front surface of the ridges, a space is present below the relatively high sites of the ridges, and the height of the space from the bottom surface is $b_1$.

8. The non-woven fabric sheet according to claim 1, wherein the back surface of the non-woven fabric sheet has a bottom surface $B_0$ and a surface $B_1$ of a height $b_1$ from the bottom surface, the bottom surface $B_0$ and the surface $B_1$ are arranged in a staggered pattern, each bottom surface $B_0$ is separated from the adjacent bottom surface $B_0$, and each surface $B_1$ is connected to four adjacent surfaces $B_1$.

9. The non-woven fabric sheet according to claim 8, wherein each bottom surface $B_0$ has a shape selected from the group consisting of square, rectangular, rhomboid, polygonal, circular and oval shapes.

10. An absorbent article that comprises the non-woven fabric sheet according to claim 1.

11. The non-woven fabric sheet according to claim 1, wherein the back surface of the non-woven fabric sheet has a bottom surface $B_0$ and surface $B_1$ of a height $b_1$ from the bottom surface, the bottom surface $B_0$ extends in a transverse direction perpendicular to the longitudinal direction and each bottom surface $B_0$ is arranged in parallel, and the space is connected in the transverse direction perpendicular to the longitudinal direction.

12. The non-woven fabric sheet according to claim 11, wherein sites where the height from the bottom surface is relatively high and relatively low sites are alternately formed along the longitudinal direction on the front surface of the ridges, a space is present below the relatively high sites of the ridges, and the height of the space from the bottom surface is $b_1$.

* * * * *